United States Patent
Pinczower (12)

(10) Patent No.: US 6,306,084 B1
(45) Date of Patent: Oct. 23, 2001

(54) APPARATUS AND METHOD FOR OBTAINING A SPECIMEN FROM A BODILY ORIFICE

(76) Inventor: Eric Pinczower, 11037 Champagne Point Rd., Kirkland, WA (US) 98034

(*) Notice: Subject to any disclaimer, the term of this patent is extended or adjusted under 35 U.S.C. 154(b) by 0 days.

(21) Appl. No.: 09/306,323

(22) Filed: May 6, 1999

(51) Int. Cl.⁷ .................................................. A61B 1/227

(52) U.S. Cl. .................. 600/184; 600/200; 604/317; 604/514

(58) Field of Search ................................... 600/184, 200; 604/514, 317

(56) References Cited

U.S. PATENT DOCUMENTS

| | | |
|---|---|---|
| 4,684,362 | 8/1987 | Holt . |
| 4,766,886 * | 8/1988 | Juhn ........................................ 128/9 |
| 4,785,796 * | 11/1988 | Mattson .................................. 128/9 |
| 5,390,663 * | 2/1995 | Schaefer ................................. 128/9 |
| 5,916,150 * | 6/1999 | Stillman ............................... 600/184 |

OTHER PUBLICATIONS

XOMED, Rhinology Products.

* cited by examiner

Primary Examiner—Linda C. M. Dvorak
Assistant Examiner—Jocelyn Debra Ram
(74) Attorney, Agent, or Firm—Knobbe Martens; Olson & Bear, LLP

(57) ABSTRACT

An apparatus and method permit a general practitioner to obtain specimens from a bodily orifice of an animal, such as, for example, a sinus specimen from a nasal area of a human. The apparatus includes a specimen access tube fixedly or removably connected to a speculum, which may be a standard nasal speculum attachment. Anti-contamination structures, either inside or outside the specimen access tube protect against contamination of the specimen due to contact with other matter in the bodily orifice. In accordance with the method, a practitioner advances the specimen access tube into the bodily orifice, and advances the speculum toward the orifice to visualize the advancement of the specimen access tube. When the tip of the specimen access tube is proximate the specimen to be collected, the practitioner advances an applicator into the end of the specimen access tube such that a head of the applicator contacts and holds the specimen. The practitioner withdraws the applicator and the specimen access tube, and places the applicator in a standard culture medium.

29 Claims, 17 Drawing Sheets

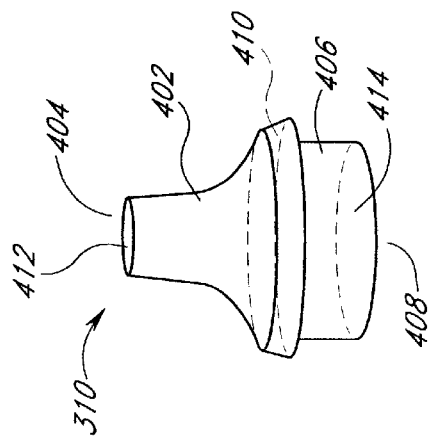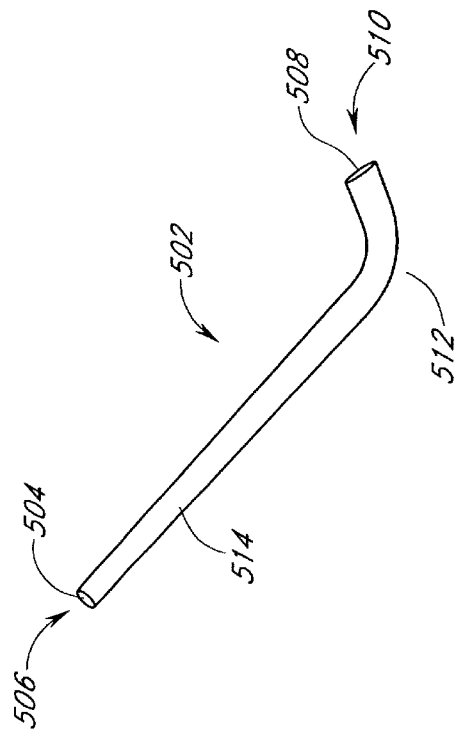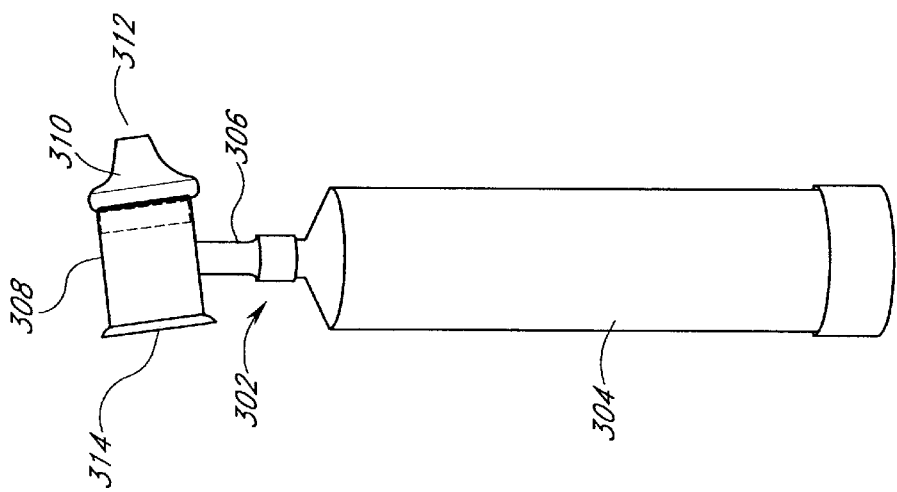

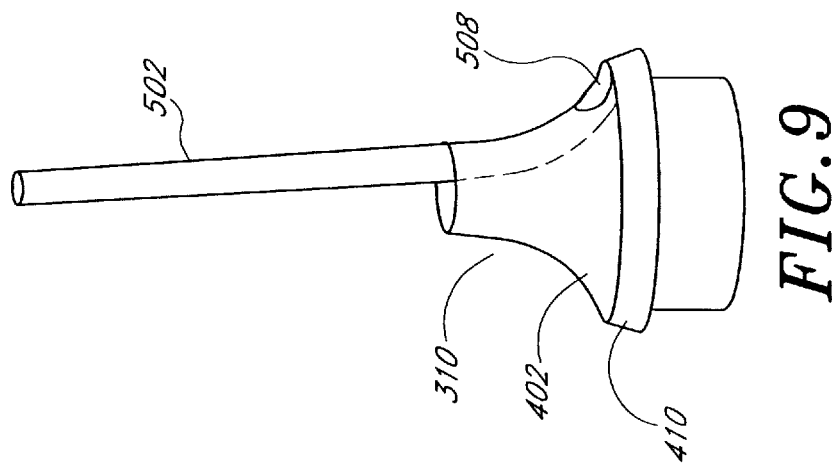
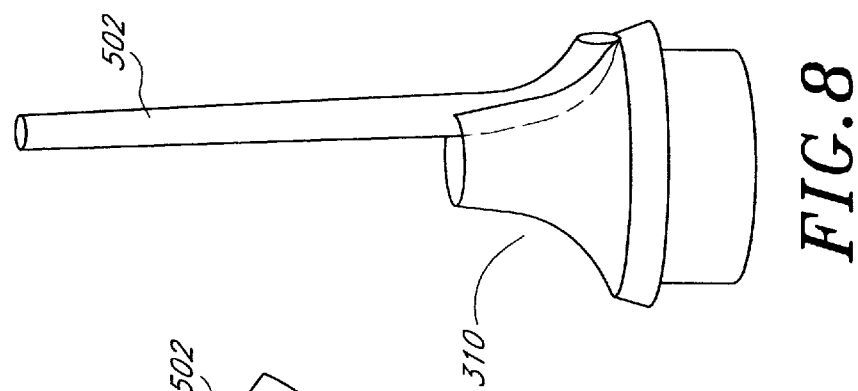
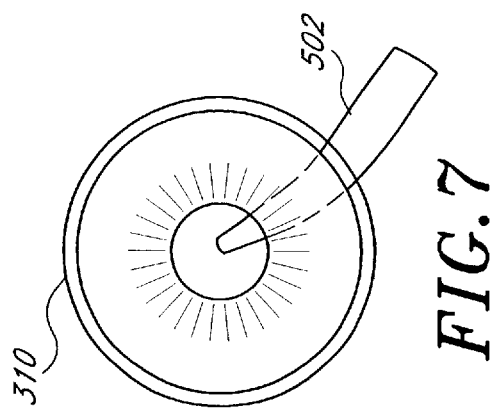
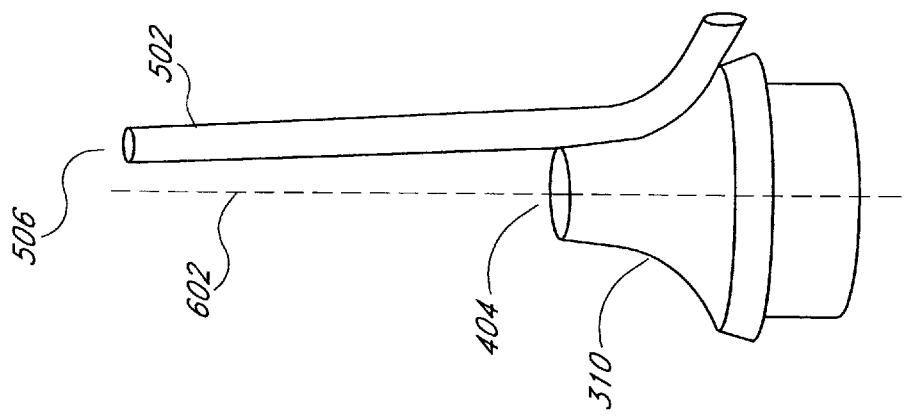

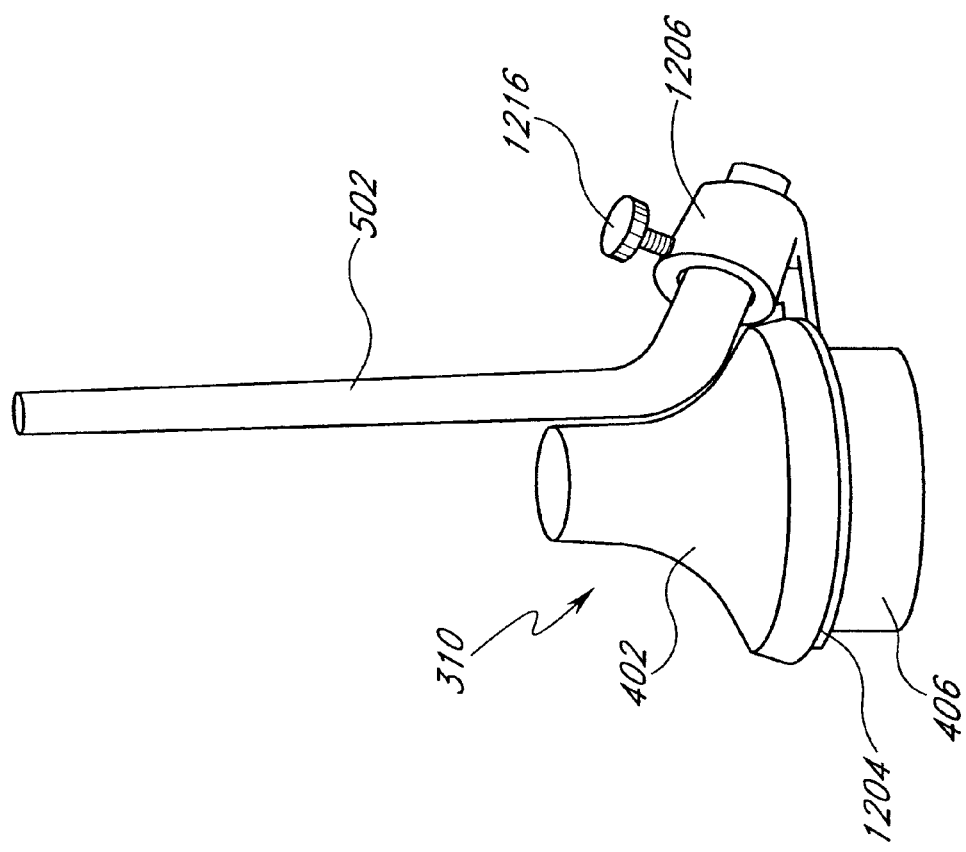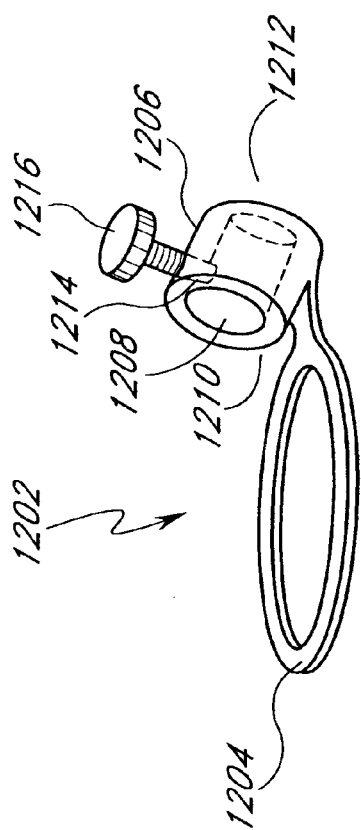

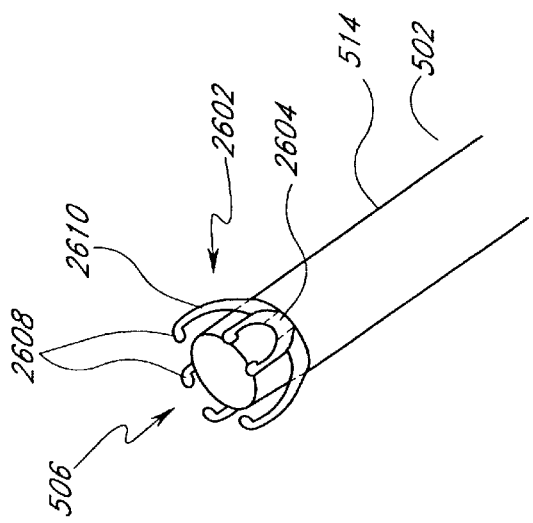
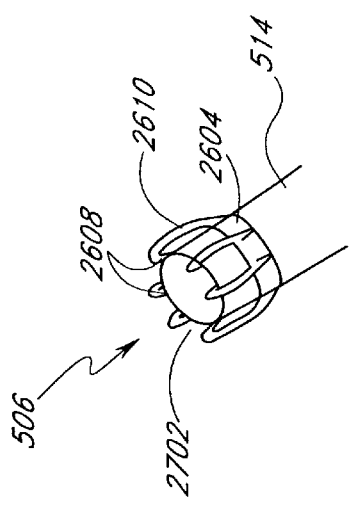
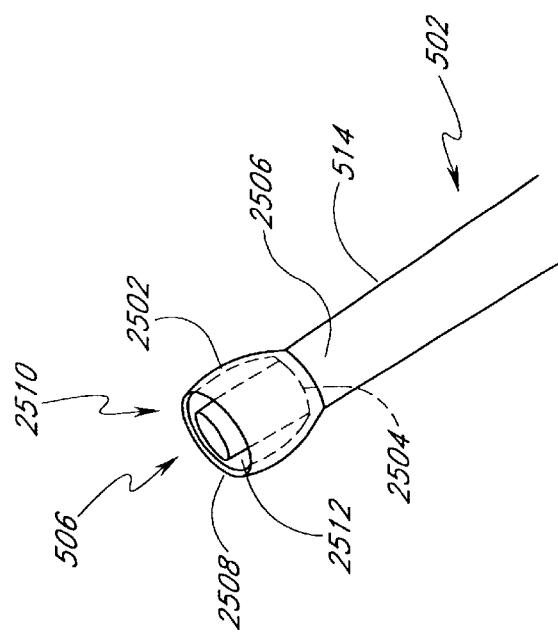
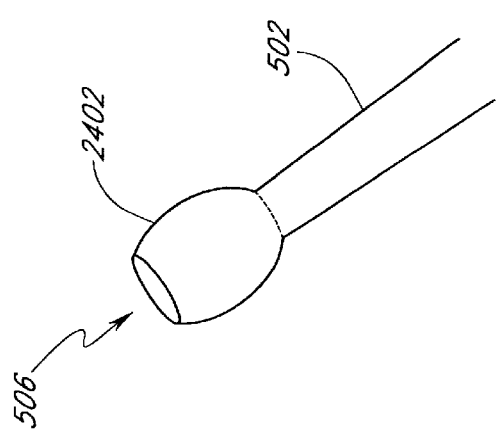

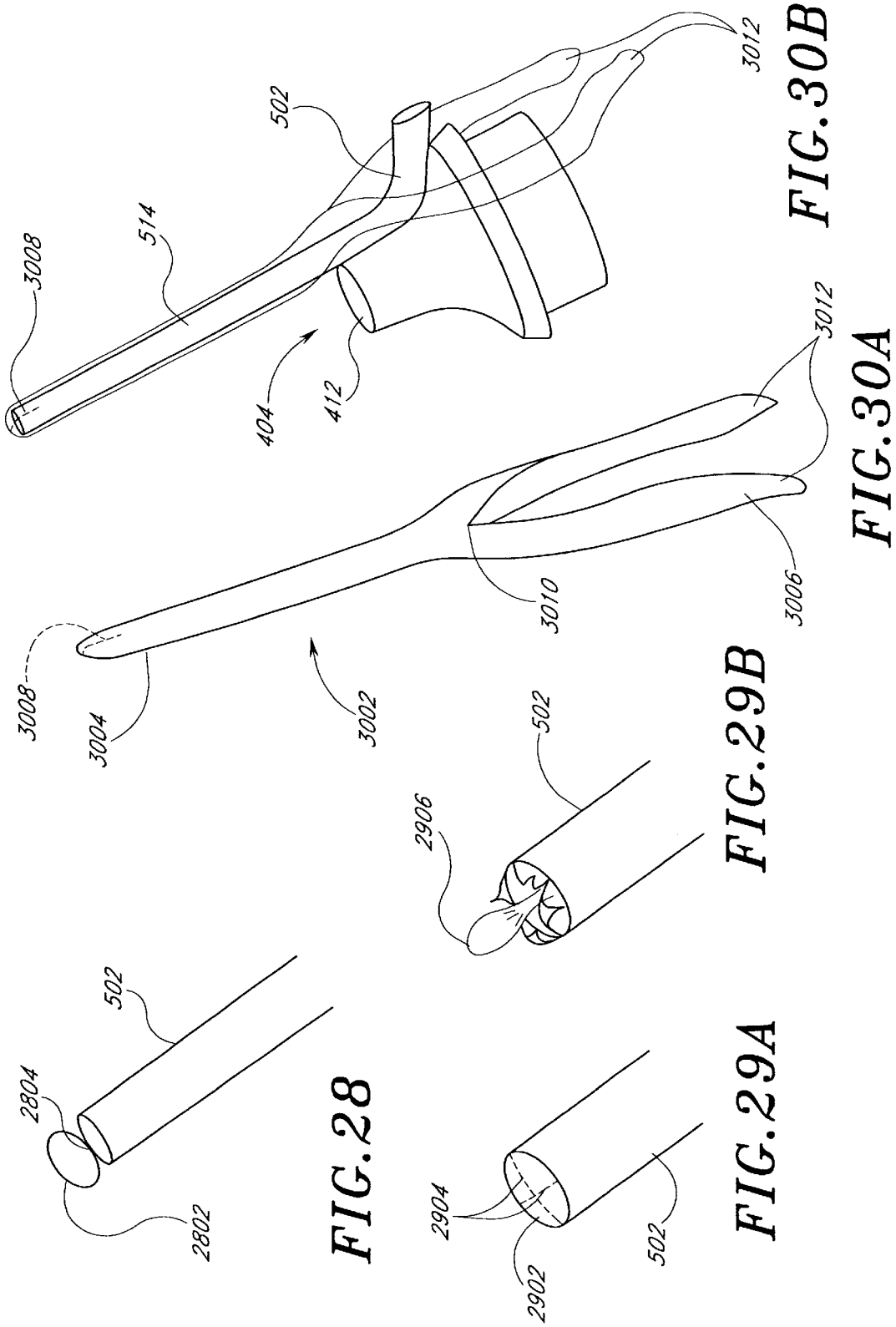

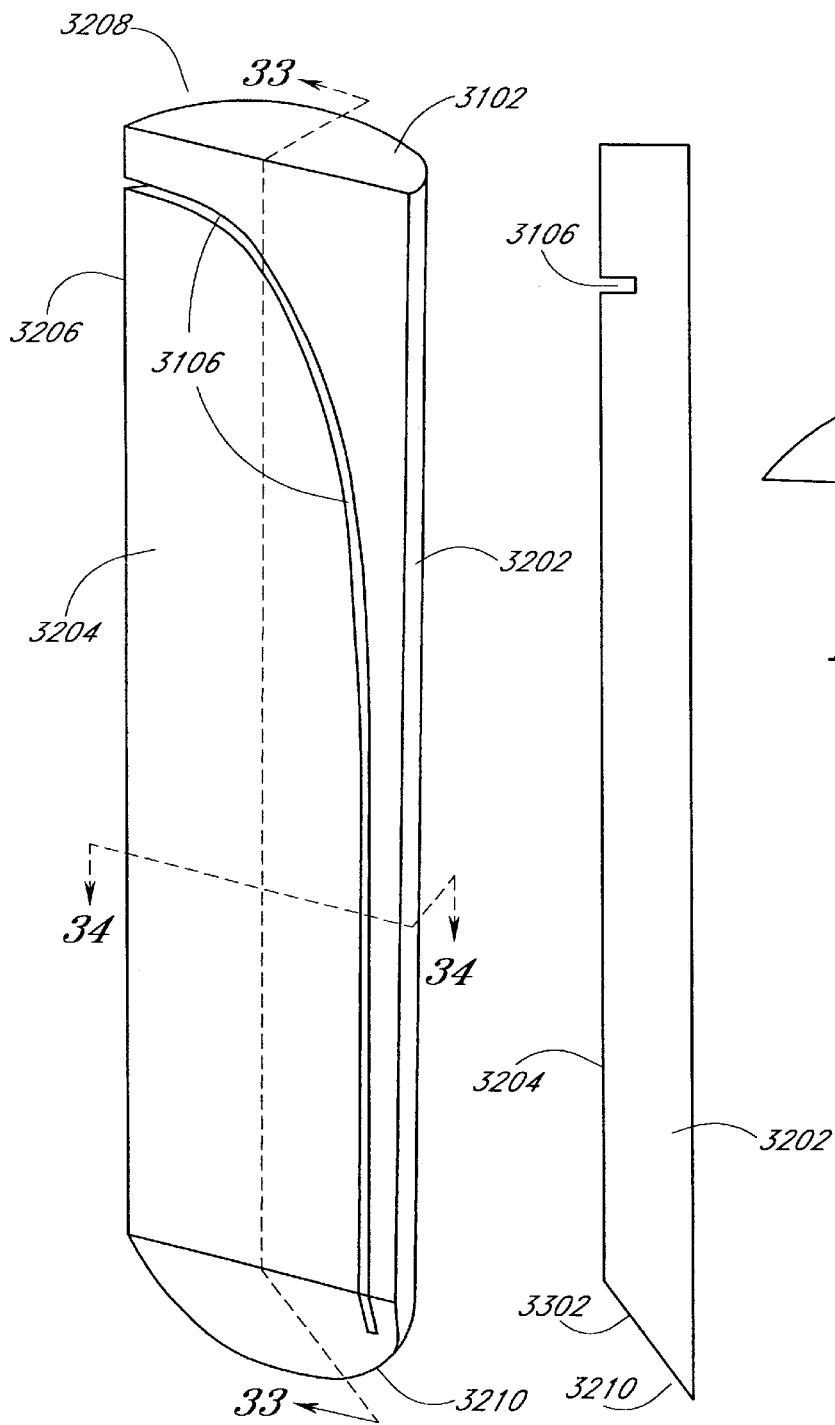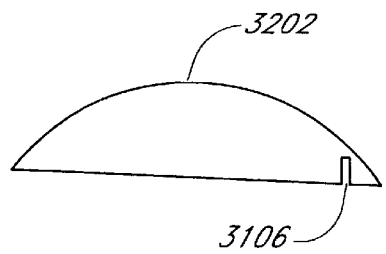
FIG.32  FIG.33  FIG.34

APPARATUS AND METHOD FOR OBTAINING A SPECIMEN FROM A BODILY ORIFICE

BACKGROUND OF THE INVENTION

1. Field of the Invention

This invention relates to the field of medical testing, and, more particularly, relates to an apparatus and method for obtaining a specimen from a bodily orifice of an animal, such as a human, which, for example, may then be analyzed or cultured to determine the presence of various organisms.

2. Description of the Related Art

Obtaining and culturing an infection provides invaluable information in the form of precise microorganism identification. That information typically enables a physician to choose and administer a form of treatment, such as a particular antibiotic, closely matched to the identified microorganism and known to be effective in treating the microorganism. Without an identification of the responsible microorganism, a physician is left with little choice but to treat an infection empirically, that is, to choose an antibiotic or other treatment that has proven effective in treating the most common organisms that cause infections. But such treatments are often suboptimal.

Before an infection may be cultured, a specimen must be obtained. Because current methods for obtaining specimens, particularly sinus-related specimens, are generally difficult and often painful and require the skills of a specialist, the benefits of a culture are, in practice, not readily available to general practitioners. Thus, infections are generally treated empirically, and, as a result, patients often receive less than optimal treatment for their infections. This is particularly true for sinus infections.

One existing technique for obtaining a sinus specimen is known as an antral tap, sometimes referred to as a canine puncture and maxillary tap. This procedure is the most common technique for obtaining a sinus culture. The antral tap procedure involves placing an instrument, such as a sturdy needle (18 gauge or thicker), or a special needle or trocar, through the face of the maxillary sinus, above the canine tooth, under the lip. The bone in this area—the canine fossa—is quite thin. The instrument is placed through the mucosa bone and the underlying sinus mucosa. Special instruments have been designed to allow rapid puncture of the bone. One such instrument, resembling a small but powerful stiletto, is designated the "sino-ject."

The antral tap procedure is an extremely painful procedure, especially in the many cases when the patient has an inflamed infected sinus. Thus, the procedure often requires general anesthesia, but, at a minimum, requires local anesthesia and sedation. As is well known, both local and general anesthesia procedures carry inherent risks. Besides pain, potential complications of the antral tap include bleeding, maxillary fracture, and even orbital or eye injuries. The antral tap procedure is limited in that it can provide a sinus specimen from the maxillary sinus only.

Another form of the antral tap procedure is similar to that described above, but is performed along the floor of the nose with penetration of the lateral nasal wall below the inferior turbinate. This form of the antral tap is just as painful, and requires a special curved needle and trocar, or other sturdy instrument, for puncture of the thin bone below the inferior turbinate. This procedure often results in severe epistaxis, with possible complications including intranasal injury, such as a persistent opening with possible chronic sinusitis, intranasal scarring, injury to the nasolacrimal duct possibly leading to epiphora or chronic tearing, or some combination of these. Both forms of antral tap must be performed by a specialist.

Another existing technique for obtaining a sinus specimen is to draw the specimen from the middle meatus (between the middle turbinate and the lateral nasal wall). The middle meatus is where the maxillary sinuses drain naturally, as do the frontal and ethmoid sinuses. While simple nasal cultures have a very low correlation with those of the maxillary sinus, cultures from the middle meatus correlate 100% with maxillary sinus cultures. This technique is useful to treat cases of maxillary sinusitis, ethmoid sinusitis and frontal sinusitis.

One primary difficulty with obtaining middle meatus specimens is contamination of the culture swab when approaching the middle meatus or when removing the swab from the middle meatus. Because of the high incidence of contaminated specimens, only skilled otolaryngologists, frequently with the aid of an endoscope, can perform the procedure with a reasonable chance for success. Moreover, with existing instruments and techniques, there is a serious risk of injury to the skull base, the brain and the orbit if the procedure is not done very carefully by a specialist.

Because of the complexity of current techniques, the serious associated risks, and the high level of skill required to obtain sinus specimens, most patients presenting with sinusitis are treated empirically. However, many studies have concluded that microorganisms are rapidly developing resistance to the most effective general antibiotics. Thus, the efficacy and availability of good empiric antibiotics is decreasing. When empiric treatments fail to stop a sinus infection, a sinus culture must be obtained. Therefore, as the effectiveness of empirical antibiotics decreases, the need for sinus cultures will increase. Moreover, many argue that all sinus infections should be cultured in the first instance.

What is needed is a technique for obtaining a specimen, and particularly a sinus specimen, that can be performed with consistent success by a general practitioner, without contamination, without substantial pain, and with minimal risk of injury to the patient.

SUMMARY OF THE INVENTION

The present invention advantageously provides an apparatus and method for obtaining a specimen, which can be performed routinely by a general practitioner, with little risk of contamination of the specimen, and with minimal pain and minimal risk of injury to the patient.

One embodiment of the present invention is an apparatus for obtaining a specimen through a bodily orifice of an animal. The apparatus comprises: (1) a speculum having an insertion end and a viewing end, said speculum defining a visualization path from said viewing end and through said insertion end, said speculum permitting visualization at said viewing end and along said visualization path of matter within said orifice when said insertion end is positioned in an opening of said orifice; and (2) a specimen access tube having an insertion end and a collection end, said specimen access tube operably connected to said speculum in an arrangement wherein said insertion end of said specimen access tube enters said orifice during said visualization, said specimen access tube defining a collection path from said collection end and through said insertion end of said specimen access tube, said specimen access tube providing access from said collection end through said collection path to a specimen within said orifice proximate to said insertion end of said specimen access tube. An aspect of the invention is one wherein said collection end of said specimen access tube remains outside said bodily orifice during said visualization and while said access to said specimen is provided. A further aspect of the invention is one wherein said collection path provides access to said specimen in a manner substantially avoiding contact with matter along bodily surfaces inside said orifice during said access. Still another aspect of the invention is one wherein at least a portion of said specimen access tube is substantially viewable from said viewing end of said speculum via said visualization path. Yet another aspect of the invention is one wherein a portion of said specimen access tube is located within a space defined by said speculum. Another aspect of the invention is one wherein said speculum is a standard speculum attachment. An additional aspect of the invention is one wherein said specimen access tube is fixedly attached to said speculum. A still further aspect of the invention is one wherein said specimen access tube is integrally formed with said speculum. Yet another aspect of the present invention is one wherein said specimen access tube is removably attached to said speculum. A further desirable aspect of the invention further comprises means for removably attaching said specimen access tube to said speculum. Another embodiment of the invention further comprises a speculum attachment ring fitting substantially securely around said speculum, said speculum attachment ring holding said specimen access tube in a first position relative to said speculum permitting said access to said specimen, and said speculum attachment ring manipulable to allow said specimen access tube to be located in a second position relative to said speculum permitting said speculum attachment ring to be fit around said speculum. A still further embodiment of the present invention further comprises anti-contamination means substantially separating matter in said orifice from said collection path during said entry of said specimen access tube into said orifice. An aspect of this embodiment is one wherein said anti-contamination means is an approximately olive-shaped structure connected at a tip of the specimen access tube at said insertion end. An alternative aspect of this embodiment is one wherein said anti-contamination means includes a thin film covering an opening in said specimen access tube at said insertion end. A further aspect of the present invention is one wherein said animal is human. Another aspect of the present invention is one wherein said orifice is proximate to a human nose. One more aspect of the present invention is one wherein said specimen is located in a middle meatus region of a human.

A method in accordance with the present invention obtains a specimen from a bodily orifice of an animal. The method comprises the steps of: (1) advancing an insertion end of a specimen access tube into said bodily orifice such that a tip of said specimen access tube at said insertion end comes to rest proximate to a specimen in said bodily orifice; (2) viewing through a speculum at least a portion of said advancing of said insertion end into said bodily orifice, said speculum operably connected to said specimen access tube; and (3) advancing a head of an applicator into a collection end of said specimen access tube and through said tip such that said head contacts and holds said specimen. In another embodiment, the method comprises the further step of withdrawing said specimen access tube from said bodily orifice. In still another embodiment, the method comprises the still further step of withdrawing said applicator head from said specimen access tube. In another embodiment, the method comprises the yet still further step of placing said applicator head in a standard culture medium. One aspect of the method is one wherein said speculum is removably connected to said specimen access tube. Another aspect of the method is one wherein said advancing of said applicator head pierces a thin film stretched across said tip, said thin film substantially preventing matter in said bodily orifice from entering said specimen access tube during said advancing of said insertion end of said specimen access tube. A still further aspect of the method is one wherein a thin film specimen access jacket envelopes a substantial portion of said insertion end of said specimen access tube, said specimen access jacket having at least one activation tab which operates when pulled to tear open a tip of said specimen access jacket covering said tip of said specimen access tube, said specimen access jacket substantially preventing matter in said bodily orifice from entering said specimen access tube during said advancing of said insertion end of said specimen access tube, and the method comprises the further step of pulling said activation tab of said specimen access jacket before said step of advancing said head of said applicator. One more aspect of the method is one wherein a blade portion of a slidable shield slides to a closed position to substantially close a hole at said tip of said insertion end of said specimen access tube and slides to an open position to substantially open said hole, wherein said slidable shield has a shaft portion extending out of the collection end of said specimen access tube, said shaft portion manipulable to cause said blade portion to open or close said hole, and the method comprises the further step of manipulating said shaft to substantially open said hole before said step of advancing said head of said applicator.

In another embodiment, the present invention is a specimen access device comprising (1) collection means for providing a specimen collection path extending from outside a bodily orifice to a position proximate to a specimen in said bodily orifice; (2) a speculum attachment operably connected to said collection means to provide visualization of a portion of said collection means in said bodily orifice; and (3) anti-contamination means substantially separating said collection means from matter in said bodily orifice other than said specimen.

BRIEF DESCRIPTION OF THE DRAWINGS

FIG. 3 illustrates a standard otoscope;

FIG. 4 illustrates a nasal speculum attachment that may be used in accordance with one embodiment of the present invention;

FIG. 5 illustrates one embodiment of a specimen access tube in accordance with one embodiment of the present invention;

FIG. 6 illustrates a representation of a specimen access tube operably attached to a nasal speculum attachment;

FIG. 7 illustrates a representation of the nasal speculum attachment attached to the specimen access tube;

FIG. 8 illustrates another embodiment of the present invention wherein the specimen access tube is partially integrally attached to the nasal speculum attachment;

FIG. 9 illustrates a representation of another embodiment of the present invention wherein a portion of the specimen access tube is located within a the nasal speculum attachment;

FIG. 12 illustrates one embodiment for an adapter for connecting the specimen access tube to the nasal speculum attachment;

FIG. 13 illustrates a representation of an adapter operably connected to the nasal speculum attachment and operably connected to the specimen access tube;

FIG. 24 illustrates a representation of a specimen access tube having an anti-contamination structure in accordance with an embodiment of the present invention;

FIG. 25 illustrates another representation of a specimen access tube having an anti-contamination structure in accordance with an embodiment of the present invention;

FIG. 26 illustrates still another representation of a specimen access tube having an anti-contamination structure in accordance with an embodiment of the present invention;

FIG. 27 illustrates another embodiment of an anti-contamination structure in accordance with the present invention;

FIG. 28 illustrates an anti-contamination lid structure in accordance with an embodiment of the present invention;

FIG. 29A illustrates another embodiment of an anti-contamination structure in accordance with the present invention; FIG. 29B illustrates the use of an embodiment of the circular film anti-contamination structure;

FIG. 30A illustrates another anti-contamination structure in accordance with an embodiment of the present invention; FIG. 30B illustrates a representation of a specimen access jacket fit over a speculum access tube in an embodiment of the present invention;

FIG. 32 illustrates a perspective view of a first shield guide side wall in accordance with an embodiment of the present invention;

FIG. 33 illustrates a side view of the shield guide side wall in accordance with an embodiment of the present invention;

FIG. 34 illustrates a cross-sectional view through the shield guide side wall in accordance with an embodiment of the present invention;

DETAILED DESCRIPTION OF THE PREFERRED EMBODIMENT

Figure 1:
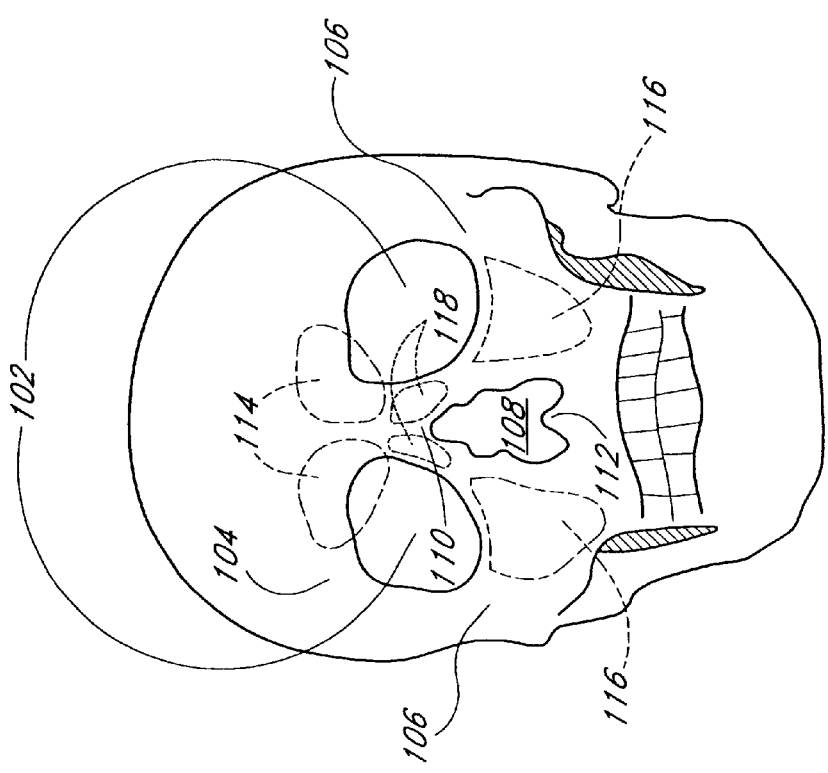
FIG. 1 is an illustration of a human skull.

FIG. 1 is an illustration of a human skull. Bilateral orbits 102 are formed in part by the frontal bone 104 and the malar bones 106. A nasal area 108 is defined in part by the nasal bone 110 and an anterior nasal spine 112.

Frontal sinuses 114 are defined by tissues and bones of the skull, the frontal sinuses 114 positioned generally behind and upward of the orbits 102. Maxillary sinuses 116 are defined by the bone and tissue of the skull on either side of the nasal area 108 and below the orbits 102. Additionally, the tissues and bones of the skull define ethmoid sinuses 118 positioned generally between the orbits 102 and the nasal area 108.

Figure 2:
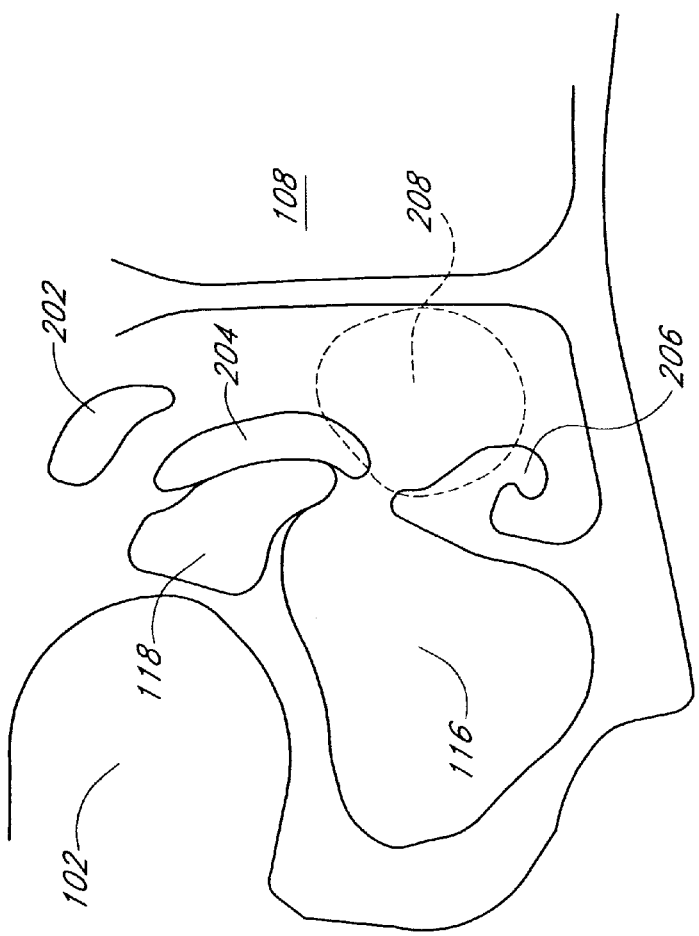
FIG. 2 illustrates an expanded view of regions in the skull proximate to the orbit and nasal area.

FIG. 2 illustrates an expanded view of regions in the skull proximate to the orbit 102 and nasal area 108. A superior turbinate bone structure 202, a middle turbinate bone structure 204, and an inferior turbinate bone structure 206 are shown by FIG. 2 in approximated form to be situated generally between the orbit 102 and the nasal area 108. The middle turbinate 204 partially defines a middle meatus region 208.

As is generally known, the frontal sinuses 114, the ethmoid sinuses 118, and the maxillary sinuses 116 drain into the middle meatus 208. As such, specimens obtained from the middle meatus 208 have a high correspondence to the state of the frontal 114, ethmoid 118, and maxillary sinuses 116. Thus, cultures performed on specimens from the middle meatus 208 can predict with high accuracy the cause of infections in the frontal 114, ethmoid 118, and maxillary sinuses 116. The present invention advantageously permits easy, sterile access to the middle meatus 208 without contamination.

Also, advantageously, the present invention works with existing equipment for examining bodily orifices. FIG. 3 illustrates a standard otoscope 302. The otoscope comprises a handle 304, which may include a source of power such as batteries, a neck 306 and a head 308. The head 308 may include magnification means (not shown) such as ground lenses and/or illumination means (not shown) such as a high intensity light bulb.

As will be appreciated by those of ordinary skill in the art, the otoscope 302 may be used by a medical practitioner to look into bodily orifices, including the inside of a human nose. When used to look into a nose, the practitioner generally places a nasal speculum attachment 310 into an access end 312 of the head 308, and then inserts the nasal speculum attachment 310 some distance into a nostril while viewing an area inside the nostril through a viewing end 314 of the head 308.

FIG. 4 illustrates a nasal speculum attachment 310 that may be used in accordance with one embodiment of the present invention. The nasal speculum attachment 310 comprises an approximately conical insertion surface 402 at an insertion end 404 of the nasal speculum attachment 310 and an approximately cylindrical fit cylinder 406 at a fit end 408 of the nasal speculum attachment 310. An approximately cylindrical fit limiting ring 410 joins the insertion surface 402 at one end and the fit cylinder 406 at another end.

In operation, a practitioner inserts the fit cylinder 406 of the nasal speculum attachment 310 into the viewing end 312 of the head 308 of the otoscope 302. The outer diameter of the fit cylinder 406 is substantially the same as the inner diameter of the cylinder of the head 308 such that the fit cylinder 406 fits snugly within the head 308. The fit limiting ring 410, having a diameter larger than the inner diameter of the head 308 and the fit cylinder 406, limits the distance that the nasal speculum attachment 310 may be inserted into the head 308. Some nasal speculum attachments 310 may have threaded fit cylinders 406 which threadingly engage threads in some otoscope head 308 cylinders. The present invention is not limited by the presence of threads on a fit cylinder 406.

The insertion surface 402, fit limiting ring 410, and fit cylinder 406 define a roughly conical hollow chamber inside the nasal speculum attachment 310, with a hole 412 at the viewing end 404 and a second hole 414 at the insertion end 408. A visualization path is formed generally along an axis running from the hole 412 at the viewing end 404 and through the second hole 414 at the insertion end 408. When the nasal speculum attachment 310 is inserted in the head 308, a practitioner inserts the insertion surface into a nostril of a patient and looks through the viewing end 314 of the otoscope 302 and through the visualization path defined by the speculum attachment 310 to examine structures inside the patient's nostril. That viewing may be enhanced by magnifying means (not shown) or illumination means (not shown) located in the otoscope head 308.

The nasal speculum attachment 310 may be constructed of plastic, stainless steel, or any other rigid material appropriate for insertion into a bodily orifice. Many such nasal specula exist in the art, and the present invention is not limited by differences from one nasal speculum attachment to another.

FIG. 5 illustrates one embodiment of a specimen access tube 502 in accordance with one embodiment of the present invention. The specimen access tube is generally tubular, such that cross sections of the specimen access tube 502 are roughly circular. However, it is contemplated that alternative embodiments of the specimen access tube 502 have cross sections which are oval, triangular, rectangular, or other shapes which do not impede the obtaining of a specimen. The specimen access tube 502 could be made of a flexible, resilient or rigid material such as, for example, a rubber, silicone, plastic or metal appropriate for insertion into a bodily orifice, and appropriate for one-time disposable use or reuse with washing and sterilization. The specimen access tube 502 could also be made from a malleable material, such as a relatively soft metal or plastic, which a practitioner could form into an advantageous configuration suitable for a particular patient's anatomy.

The specimen access tube 502 defines a passageway or collection path running from a hole 504 at an insertion end 506 to another hole 508 at a collection end 510. A bend 512 in the specimen access tube 502 is positioned between a substantially straight shaft portion 514 and the collection end 510, and conforms generally to a non-linear slope of the insertion surface 402 of the nasal speculum attachment 310. The specimen access tube 502, in alternative embodiments, could also be straight or substantially straight.

FIG. 6 illustrates a representation of a specimen access tube 502 operably attached to the nasal speculum attachment 310. In that attachment, the insertion end 506 of the specimen access tube 502 is arranged to point away from the insertion end 404 of the nasal speculum attachment 310. The shaft portion 514 of the specimen access tube 502 is arranged to be substantially parallel to a central axis 602 defined by a straight line intersecting the centers of the hole 414 and the hole 412 of the nasal speculum attachment 310. In a preferred embodiment of the present invention, the tip of the shaft portion shaft 514 at the insertion end 506 of the specimen access tube 502 is arranged proximate to or intersecting the central axis 602.

FIG. 7 illustrates a representation of the nasal speculum attachment 310 attached to the specimen access tube 502, the arrangement viewed from the fit end 408 of the nasal speculum attachment 310. The tip of the shaft portion 514 of the specimen access tube 502 is visible through the hole 412 at the insertion end 404 of the nasal speculum attachment 310, the hole 412 being visible when looking substantially directly into the hole 414 of the nasal speculum attachment 310. Thus, the arrangement advantageously permits a practitioner to view the tip of the specimen access tube 502 in relation to bodily anatomy viewed contemporaneously through the nasal speculum attachment 310.

FIG. 8 illustrates another embodiment of the present invention wherein the specimen access tube 502 is partially integrally attached to the nasal speculum attachment 310. In the configuration shown in FIG. 8, a portion of the specimen access tube 502 proximate to the bend 512 is located within the substantially conical space defined by the nasal speculum attachment 310. This embodiment advantageously works in orifices having smaller openings, and may result in less stretching or distortion of bodily tissue to permit introduction of the specimen access tube 502.

FIG. 9 illustrates a representation of another embodiment of the present invention. In this embodiment, a portion of the specimen access tube 502 proximate to the bend 512 is located completely within the approximately conical space of the nasal speculum attachment 310. In this embodiment, the insertion surface 402 of the nasal speculum attachment 310 is interrupted by the hole 508. It will be appreciated that the hole 508 could also interrupt a portion of the fit limiting ring 410. The embodiment advantageously works in orifices with small openings and may further reduce any stretching, distortion or displacement of tissue during insertion of the specimen access tube 502.

In a preferred embodiment, the invention is used to obtain a specimen from the middle meatus 208 (FIG. 2) region of a human and potentially other areas of the nose, specifically the sphenoethmoid recess, the sphenoid sinus, the maxillary sinus, the superior and inferior meati and the frontal recess. It is contemplated, however, that the present invention is useful for obtaining any specimen from a bodily orifice of a human or other animal, and the present invention is not limited to the particular embodiments disclosed herein.

Method of Operation

In accordance with the system and method of the present invention, a patient prepares by gently blowing to clear the nose. A practitioner then decongests the patient's nose, preferably by applying two (2) puffs of oxymetazoline. It will be appreciated that other decongestants may be used. The practitioner then anesthetizes the patient's nose, preferably using a few drops of four percent (4%) lidocaine. Again, other anesthetics of substantially equivalent effect may be used.

A practitioner then inserts a flexible sterile cotton-tipped applicator in the collection end of the specimen access tube 502, and pushes the applicator therethrough so that the cotton tip rests just short of extension through the hole 504 at the insertion end 506 of the specimen access tube 502. Preferably, the applicator is a sterile urethrogenital calcium alginate tipped applicator, having a soft aluminum shaft. It will be appreciated however that other applicators suitable for collecting a specimen may be used.

Figure 10:
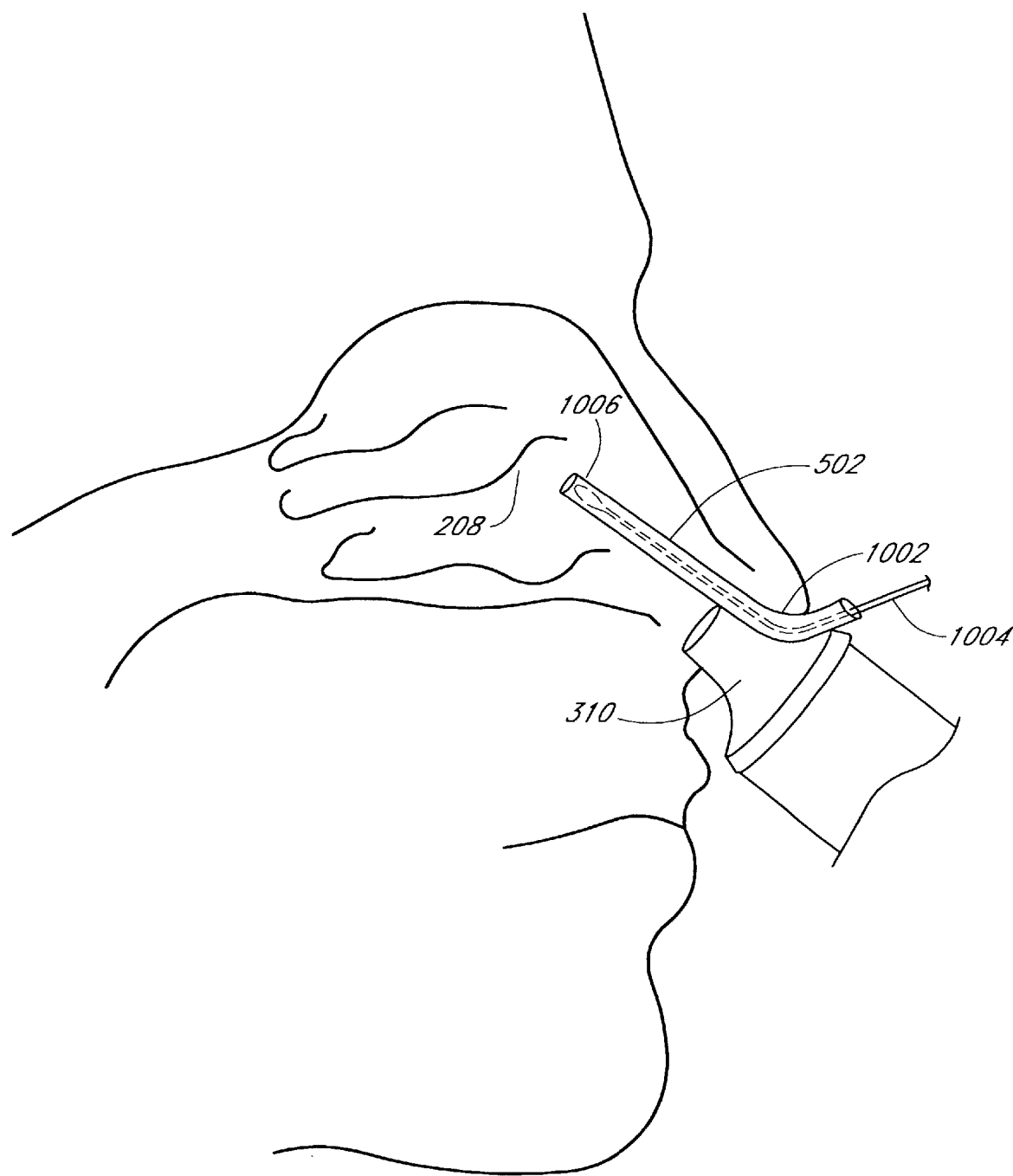
FIG. 10 illustrates a representation of the device of the present invention positioned for use in a patient.

FIG. 10 illustrates a representation of the device of the present invention positioned for use in a patient. In such position, the nasal speculum attachment 310 and the attached specimen access tube 502 are inserted through a nostril 1002 of the patient. The practitioner manipulates the tip of the specimen access tube 502 at the insertion end 506 into a position near or in the middle meatus 208.

Having previously been inserted partially within the specimen access tube 502, a portion of a sterile cotton-tipped applicator 1004 is located outside the hole 508 at the collection end 510 of the specimen access tube. The remainder of the applicator 1004 is positioned inside the specimen access tube 502 with the tip of the applicator 1006 resting substantially at and within the tip at the insertion end 506 of the specimen access tube 502.

Figure 11:
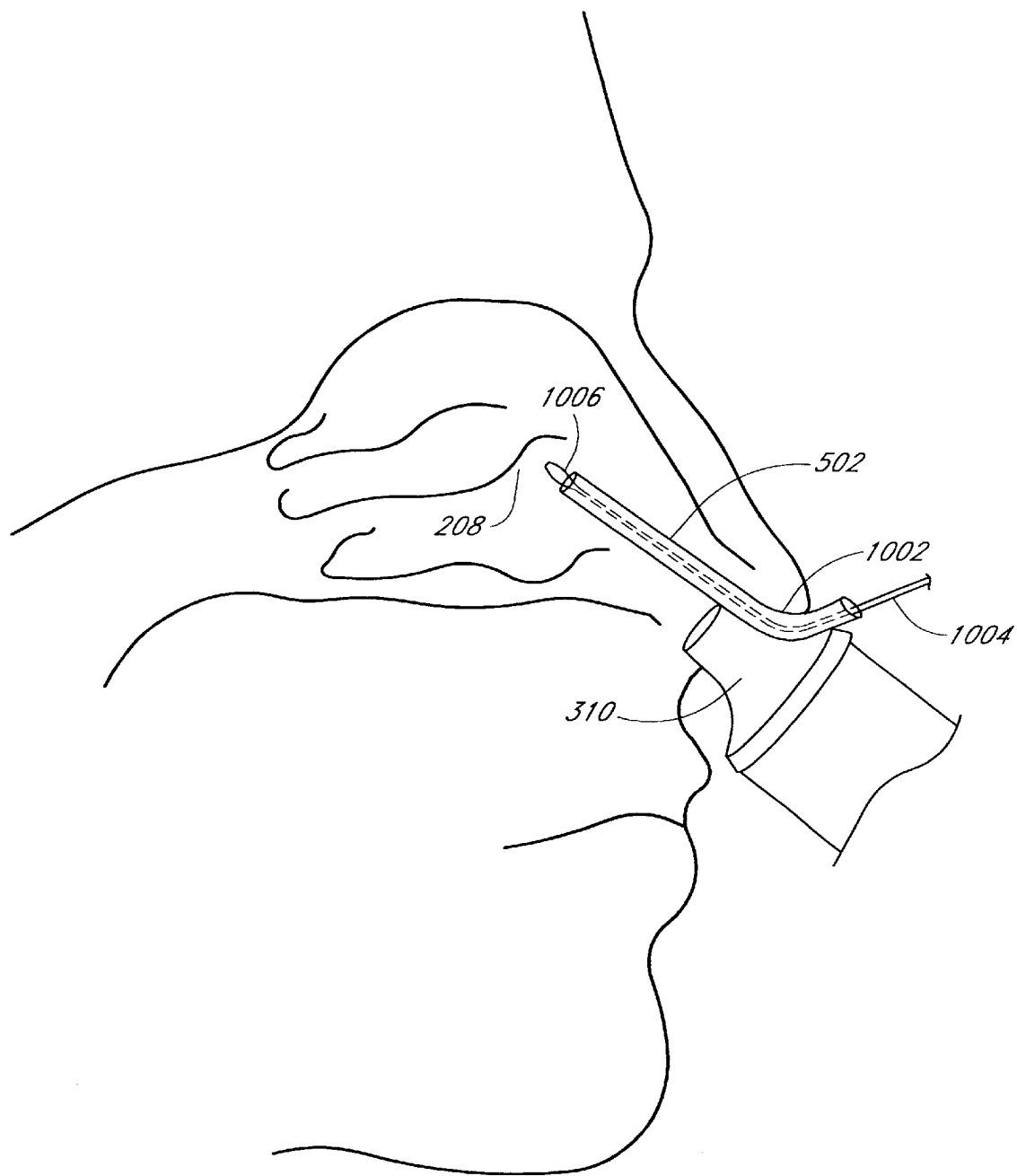
FIG. 11 illustrates a representation of an embodiment of the present invention in use in a patient.

FIG. 11 illustrates a representation of the system and method of the present invention in use. To collect a specimen, the practitioner advances the applicator 1004 by gently and slowly pushing the applicator into the specimen access tube 502 so that the tip 1006 of the applicator emerges from the hole 504 of the specimen access tube to contact the surface of the middle meatus 208. The practitioner then withdraws the applicator 1004 so that the tip 1006 of the applicator again comes to rest substantially at and within the tip of the specimen access tube 502 at the insertion end 506.

With the applicator 1004 withdrawn into the specimen access tube 502, the practitioner removes the nasal speculum attachment 310 and the attached specimen access tube 502 from the nose of the patient. The practitioner then removes the applicator from the specimen access tube 502, and places it in a standard culture medium. It will be appreciated that any culture medium effective to culture a specimen may be used.

It is specifically contemplated that the specimen access tube 502 could be embodied in various configurations and sizes permitting, on the one hand insertion into the anterior nares area and allowing passage of the flexible applicator or swab, preferably providing some resistance so the applicator does not fall out of the specimen access tube 502 unsupported, and on the other hand, permitting operable connection of the specimen access tube to a nasal speculum attachment 310. In some embodiments, the entire specimen access tube 502 may be substantially straight or arced to varying degrees.

In some embodiments of the present invention, such as, for example, those illustrated in FIGS. 6, 8 and 9, the specimen access tube 502 is fixedly attached to the nasal speculum attachment 310. Such attachment may be accomplished using a welding or soldering technique, by epoxy or cement, or by integral or molded formation, or by other substantially permanent means of attachment known in the art.

In additional embodiments, the specimen access tube 502 may be removeably connected to the nasal speculum attachment 310.

FIG. 12 illustrates one embodiment for an adapter for connecting the specimen access tube 502 to the nasal speculum attachment 310. The adapter 1202 comprises a speculum attachment ring 1204 having an inner diameter substantially the same as the outer diameter of the fit cylinder 406 of the nasal speculum attachment 310.

The speculum attachment ring 1204 is connected to a tube housing 1206. The tube housing is substantially cylindrical having a bore 1208 there through. In a preferred embodiment, the bore is substantially conical, the bore 1208 having a larger diameter at a speculum end 1210 of the housing 1206 and a smaller diameter at a collection end 1212 of the housing 1206. The diameter of the bore 1208 at the collection end 1212 is substantially the same as the outer diameter of the collection end of the specimen access tube 502. The housing 1206 includes a transverse threaded bore 1214 which threadingly receives a set screw 1216.

A practitioner uses the adapter 1202 by fitting the speculum attachment ring 1204 over the fit cylinder 406 of the nasal speculum attachment 310, and advancing the speculum attachment ring 1204 into contact with the fit limiting ring 410 of the nasal speculum attachment 310. It will be appreciated that the internal walls of the speculum attachment ring 1204 could be threaded to threadingly engage threaded fit cylinders 406 of certain nasal speculum attachments 310.

The practitioner then inserts the collection end of the specimen access tube 502 into the speculum end 1210 of the housing 1206 and advances the collection end of the specimen access tube 502 through the bore 1208 until it extends out of the collection end of the housing 1206, and until the bend 512 in the specimen access tube 502 is in substantial conformance with the slope of the insertion surface 402 of the nasal speculum attachment 310. The practitioner then rotates the set screw 1216 to threadingly engage the bore 1214 and to advance through said bore into contact with and to firmly position the specimen access tube 502.

FIG. 13 illustrates a representation of the adapter 1202 operably connected to the nasal speculum attachment 310 and operably connected to the specimen access tube 502. It will be appreciated that the thickness of the speculum attachment ring 1204 is sufficient to substantially prohibit movement of the adapter relative to the nasal speculum attachment 310. It will further be appreciated that the set screw 1216 is rotationally advanced into contact with the specimen access tube with a force sufficient to substantially prohibit movement of the specimen access tube 502 relative to the nasal speculum attachment 310. It will be noted that, even with the speculum attachment ring 1204 fitted over it, a sufficient height of the fit cylinder 406 extends from the speculum attachment ring 1204 to fit securely within the cylinder of the head 308 of the otoscope 302.

Figure 14:
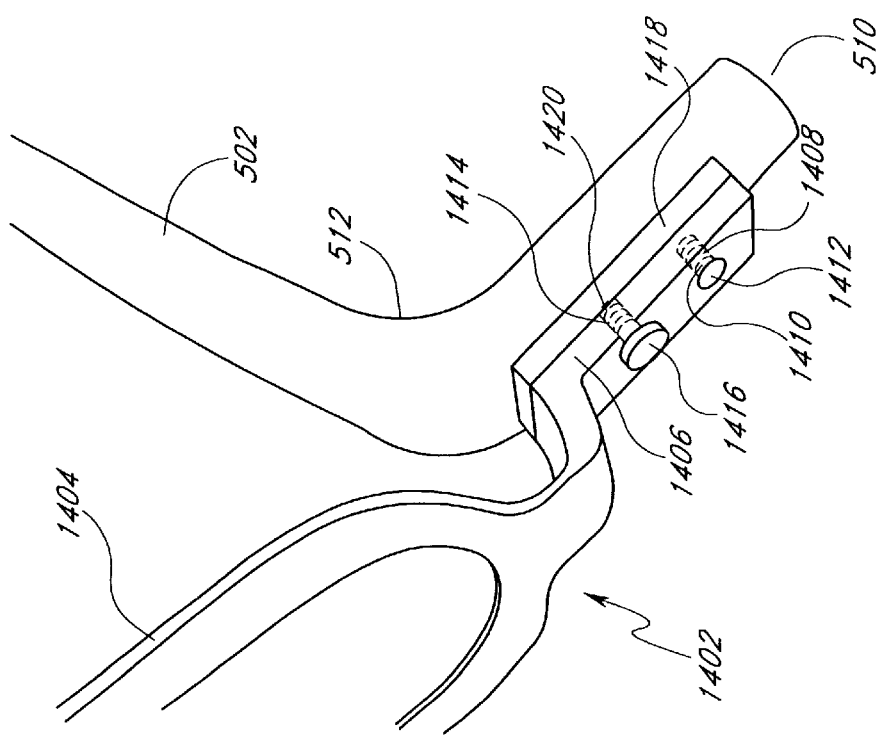
FIG. 14 illustrates a representation of another embodiment of a speculum adapter operably connected to a specimen access tube.

FIG. 14 illustrates a representation of another embodiment of a speculum adapter 1402 operably connected to a specimen access tube 502. In this embodiment, a speculum attachment ring 1404 having a dimension and configuration similar to that of the speculum attachment ring 1204, is integrally formed with, or otherwise attached to a swivel plate 1406. A pivot bore 1408 runs through the swivel plate 1406 and receives pivot pin 1410 having a diameter substantially the same as the pivot bore 1408. A pivot pin cap 1412 is fixedly attached to the pivot pin 1410, the pivot pin cap having a diameter larger than the pivot pin 1410 to engage a surface of the swivel plate 1406.

A set bore 1414 runs through the swivel plate 1406, preferably at a position between the pivot bore 1408 and the speculum attachment ring 1404. The set bore 1414 is threaded to threadingly engage a set screw 1416.

A second swivel plate 1418 is fixedly attached to the specimen access tube 502, preferably at a position between the bend 512 and the collection end 510 of the specimen access tube. The pivot pin 1410 is fixedly attached to the second swivel plate 1418 to substantially align sides of the swivel plates 1406 and 1418. A set bore 1420 runs through the second swivel plate 1418. The set bore 1420 is positioned to align with the set bore 1414 and to threadingly receive the set screw 1416 in that alignment.

In operation, a practitioner loosens the set screw 1416 by rotating it counterclockwise, such that it is no longer engaged by the set bore 1420, but remains engaged by the set bore 1414. The practitioner then pivots the specimen access tube 502 with respect to the speculum attachment ring 1404 about the pivot pin 1410 in an amount sufficient to permit fitting the speculum attachment ring 1404 onto the fit cylinder 406 (FIG. 4).

Figure 15:
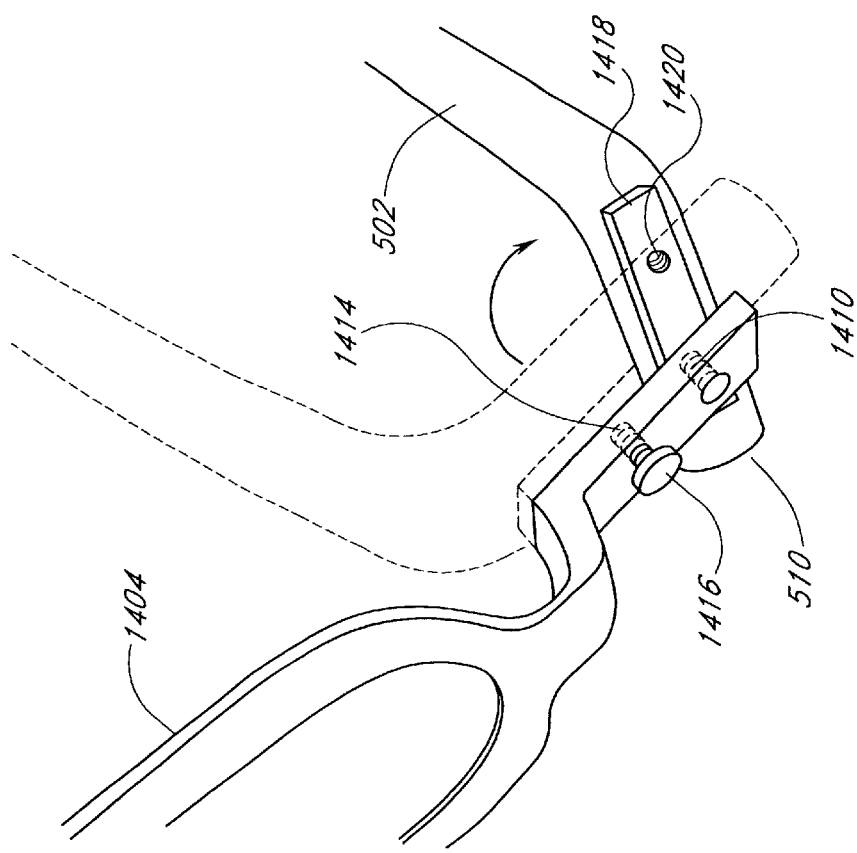
FIG. 15 illustrates pivoting of a specimen access tube with respect to a speculum attachment ring in accordance with one embodiment of the present invention.

FIG. 15 illustrates the pivoting of the specimen access tube 502 with respect to the speculum attachment ring 1404 about the pivot pin 1410 in accordance with one embodiment of the present invention.

Once the speculum attachment ring 1404 is fit onto the fit cylinder 406, the practitioner pivots the specimen access tube 502 with respect to the speculum attachment ring 1404 about the pivot pin 1410 to bring the set bore 1420 into alignment with the set bore 1414. The practitioner then rotates the set screw 1416 in a clockwise manner to threadingly engage the set bore 1420 and thereby fix the position of the specimen access tube 502 with respect to the speculum attachment ring 1404. The practitioner may then place the fit cylinder 406 into the otoscope head 308 and use the specimen access tube 502 as connected to the nasal speculum attachment 310 to collect a sinus specimen in the manner described herein.

Figure 16:
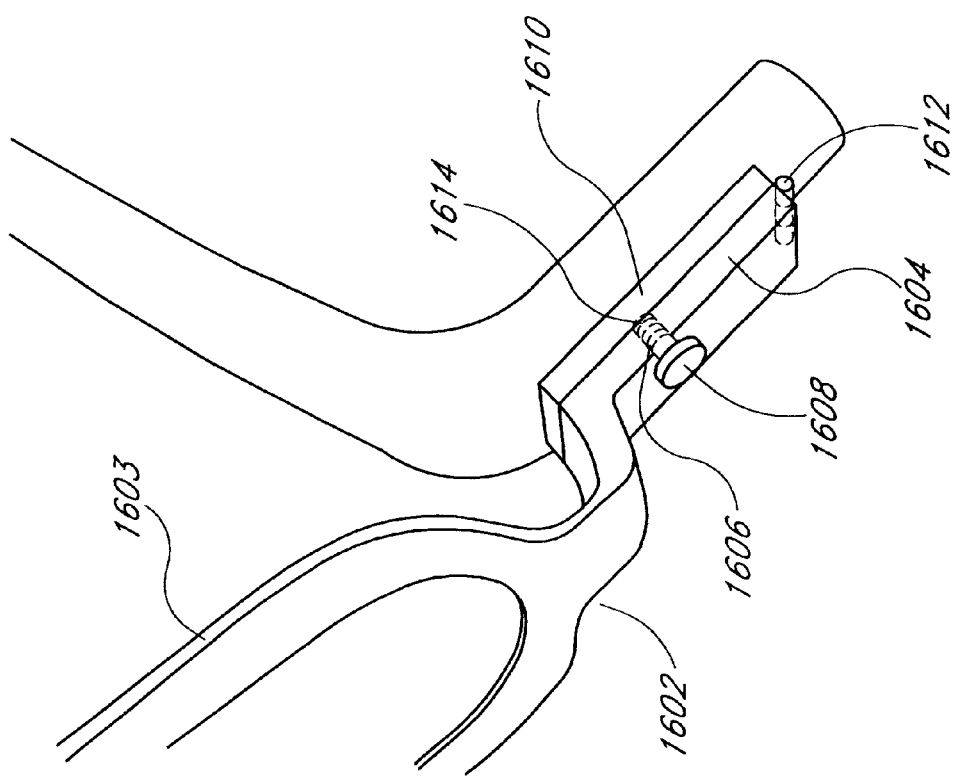
FIG. 16 illustrates another embodiment of a speculum adapter operably connected to a specimen access tube.

FIG. 16 illustrates another embodiment of a speculum adapter 1602 operably connected to a specimen access tube 502. The speculum adapter 1602 includes a speculum attachment ring 1603 integrally formed with or otherwise connected to a hinge plate 1604. A set bore 1606 runs through the hinge plate 1604, and is threaded to threadingly engage a set screw 1608.

A second hinge plate 1610 is fixedly, or otherwise attached to the specimen access tube 502, preferably at a position between the bend 512 and the collection end 510 of the specimen access tube 502. A hinge 1612 attaches the hinge plates 1604 and 1610 at ends of the hinge plates 1604 and 1610 proximate to the collection end 510 of the specimen access tube 502. A second set bore 1614 runs through the second hinge plate 1610 and is positioned to align with the set bore 1606 to threadingly receive the set screw 1608.

A practitioner uses the speculum adapter 1602 by loosening the set screw 1608 (i.e., rotating it counterclockwise), to a position wherein it is no longer engaged by the set bore 1614, but remains threadingly engaged by the set bore 1606. The practitioner then pivots the specimen access tube 502 with respect to the speculum attachment ring 1603 about the hinge 1612 in an amount sufficient to permit fitting the speculum attachment ring 1603 onto the fit cylinder 406 (FIG. 4).

Figure 17:
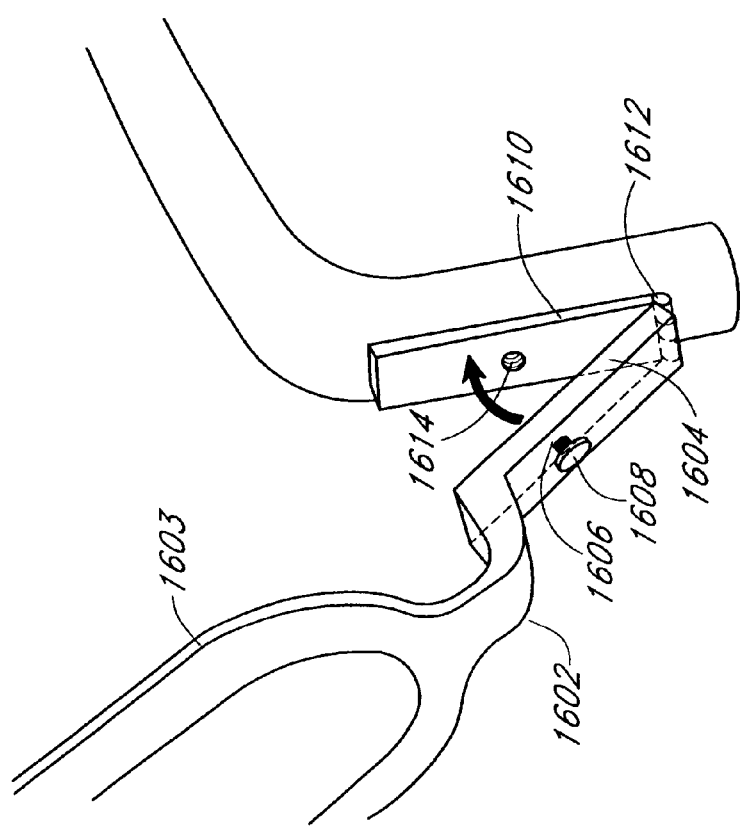
FIG. 17 illustrates pivoting of a specimen access tube with respect to a speculum attachment ring about a hinge in accordance with an embodiment of the present invention.

FIG. 17 illustrates the pivoting of the specimen access tube 502 with respect to the speculum attachment ring 1603 about the hinge in accordance with one embodiment of the present invention.

Once the speculum attachment ring 1603 is fit onto the fit cylinder 406, the practitioner pivots the specimen access tube 502 with respect to the speculum attachment ring 1603 about the hinge 1612 to bring the set bore 1614 into alignment with the set bore 1606. The practitioner then rotates the set screw 1608 in a clockwise direction to threadingly engage the set bore 1614 to thereby fix the position of the specimen access tube 502 with respect to the speculum attachment ring 1603. The practitioner may then position the fit cylinder 406 within the otoscope head 308 and use the nasal speculum attachment 310 as combined with the specimen access tube 502 to collect a sinus specimen in the manner described herein.

Figure 18:
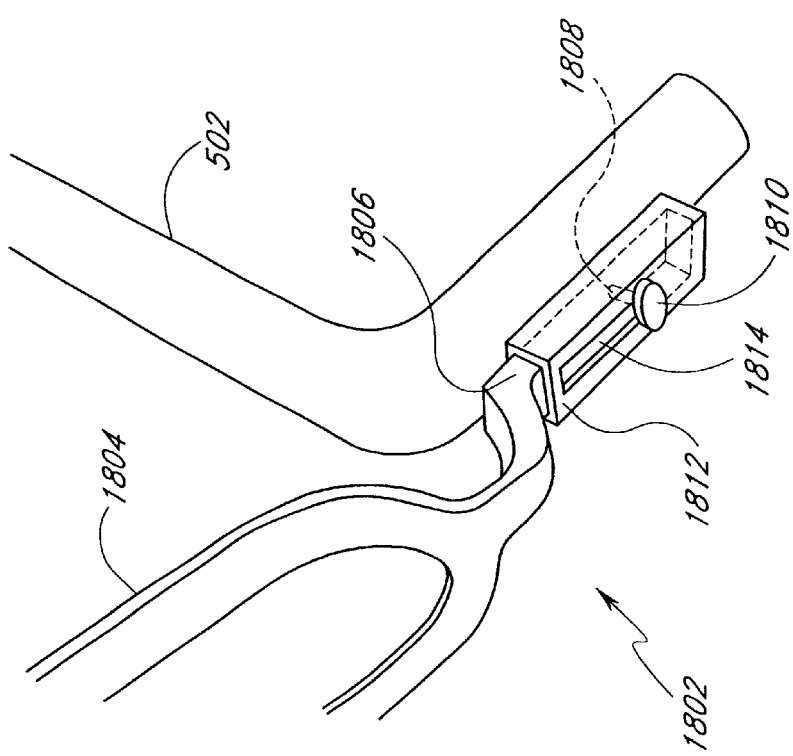
FIG. 18 illustrates a representation of another embodiment of a nasal speculum adapter in accordance with the present invention.

FIG. 18 illustrates another embodiment of a nasal speculum adapter 1802 in accordance with the present invention. A speculum attachment ring 1804 is integrally formed with or otherwise attached to a slide member 1806. A set bore 1808 runs through the slide member 1806 and is threaded to threadingly engage a set screw 1810. The set bore 1808 is positioned approximately midway along the length of the slide member 1806.

A slide housing 1812 is fixedly or otherwise attached to the specimen access tube 502, preferably at a position between the bend 512 and the collection end 510. The slide housing 1812 defines an internal passage having a rectangular cross-section of substantially the same height and width of a cross-section of the slide member 1806, thus permitting insertion of the slide member 1806 into slide housing 1812 and slidable movement of the slide member 1806 within the slide housing 1812. It will be appreciated that the cross sections of both the slide member 1806 and the internal passage of the slide housing 1812 could be of a different shape, such as, for example, circular, triangular, etc., and it is contemplated that different cross-section shapes are within the scope of the present invention.

A slot 1814 interrupts an outer surface of the slide housing 1812 on a side away from the specimen access tube 502. The slot 1814 permits access into the internal passage of the slide housing 1812.

The shaft of the set screw 1810 extends through the slot 1814 to threadingly engage the set bore 1808 in the slide member 1806. The diameter of the head of the set screw 1810 is greater than the width of the slot, and thus, when tightened, engages the outer surface of the slide housing 1812 and thereby prevents slidable movement of the slide member 1806 within the slide housing 1812.

A practitioner uses the speculum adapter 1802 by loosening the set screw 1810, preferably without removing it from the set bore 1808. The practitioner may then slide the specimen access tube 502 and slide housing 1812 attached thereto, in a direction away from the speculum attachment ring 1804 for a distance sufficient to permit the speculum attachment ring 1804 to be fit over the fit cylinder 406.

Figure 19:
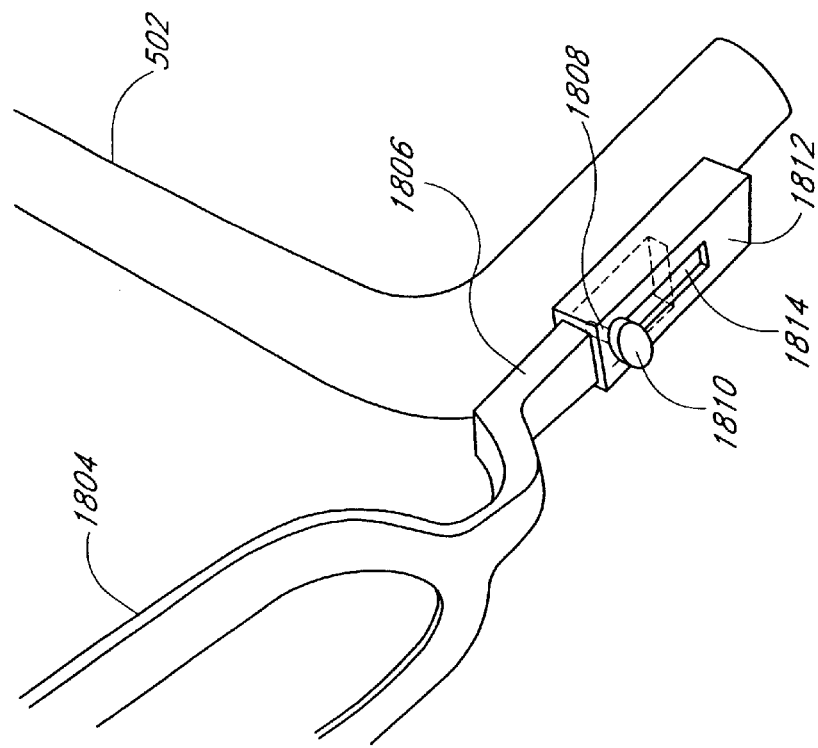
FIG. 19 illustrates a specimen access tube and slide housing positioned away from a speculum attachment ring in accordance with an embodiment of the present invention.

FIG. 19 illustrates the specimen access tube 502 and slide housing 1812 positioned away from the speculum attachment ring 1804 in accordance with an embodiment of the present invention.

Once the practitioner has fit the speculum attachment ring 1804 over the fit cylinder 406, the practitioner slides the specimen access tube 502 toward the speculum attachment ring 1804 into an operable position. The practitioner then tightens the set screw 1810 to substantially fix the specimen access tube 502 in an operable position relative to the speculum attachment ring 1804. The practitioner then positions the fit cylinder 406 within the head 308 of the otoscope 302. The practitioner may then collect a sinus sample as described herein.

Figure 20:
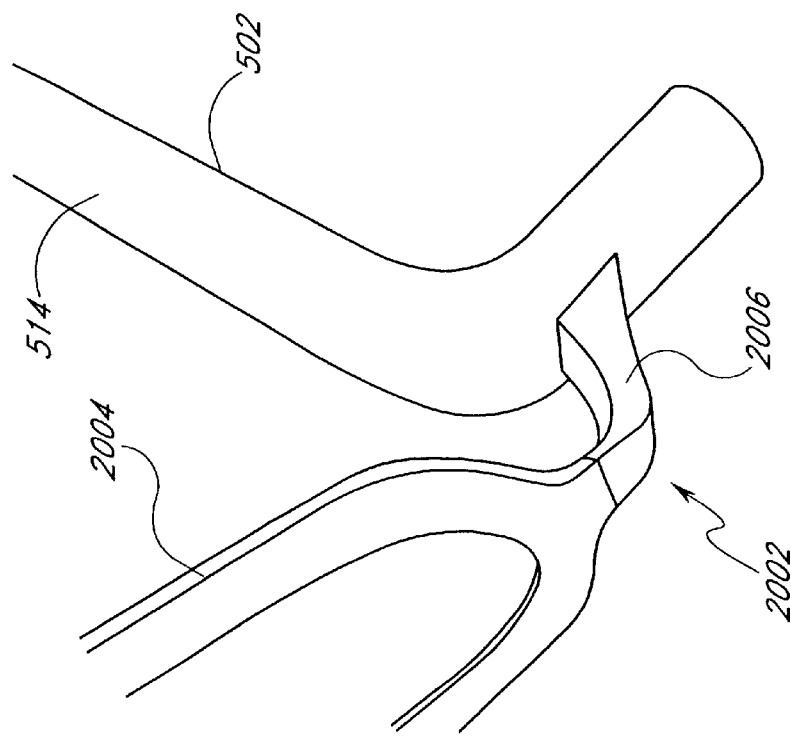
FIG. 20 illustrates another embodiment of a nasal speculum adapter in accordance with the present invention.

FIG. 20 illustrates another embodiment of a nasal speculum adapter 2002 in accordance with the present invention. A speculum attachment ring 2004 is integrally formed with or otherwise attached to an adapter neck 2006. The adapter neck 2006 is fixedly or otherwise attached to the specimen access tube 502. The adapter neck 2006 is made from a material, such as a resilient or rubberized plastic, or a hardened metal, having resiliency or memory sufficient to hold the specimen access tube 502 substantially fixed relative to the speculum attachment ring 2004 in the absence of a force tending to drive the tip of the specimen access tube 502 at the insertion end 506 away from the speculum attachment ring 2004.

A practitioner uses the speculum adapter 2002 by applying force to the specimen access tube 502 generally along its shaft portion 514 in a direction away from the speculum attachment ring 2004. This force causes the adapter neck 2006 to flex, thereby permitting the specimen access tube 502 to separate from the speculum attachment ring 2004. The adapter neck 2006 may flex primarily in a direction wherein the specimen access tube 502 moves either away from or toward the speculum attachment ring 2004, or primarily in a twisting manner about an axis substantially perpendicular to a plane defined by the circular surface of the speculum attachment ring 2004, or may flex substantially in both of those directions.

Figure 21:
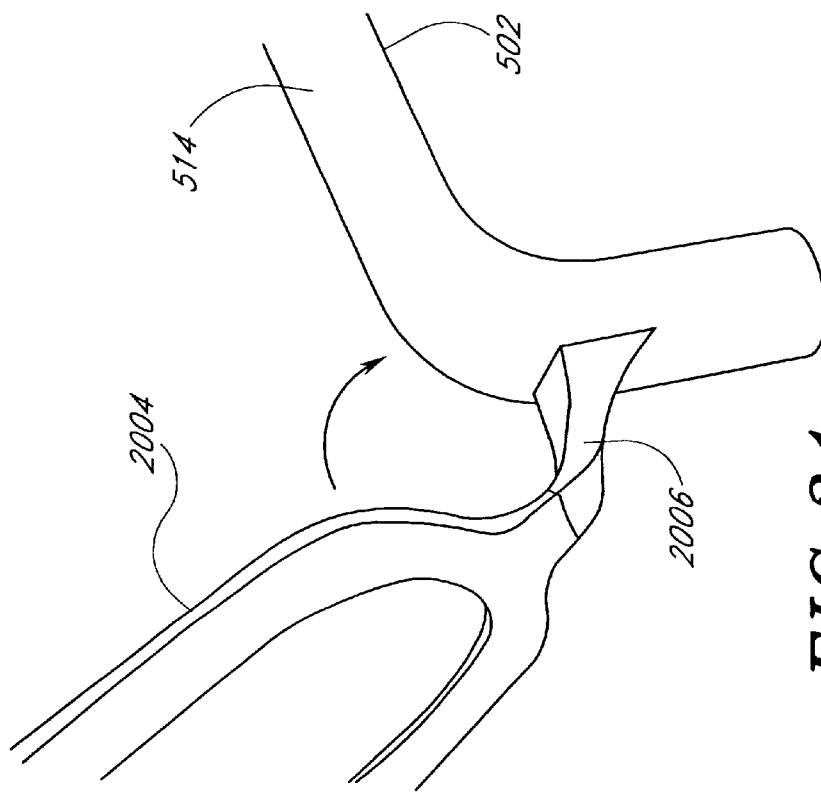
FIG. 21 illustrates a specimen access tube separated from a speculum attachment ring by way of a flexing adapter neck in accordance with an embodiment of the present invention.

FIG. 21 illustrates the specimen access tube 502 separated from the speculum attachment ring 2004 by way of flexing of the adapter neck 2006, in accordance with an embodiment of the present invention. When the specimen access tube 502 is sufficiently separated from the speculum attachment ring 2004, the practitioner fits the speculum attachment ring over the fit cylinder 406 of the nasal speculum attachment 310. The practitioner may then remove the force applied to the shaft portion 514 of the specimen access tube 502, causing the specimen access tube 502 to spring back into an operable position relative to the speculum attachment ring 2004. The practitioner may then place the fit cylinder 406 within the head 308 of the otoscope 302, and use the combined specimen access tube 502 and nasal speculum attachment 310 to collect a sinus specimen as described herein.

Figure 22:
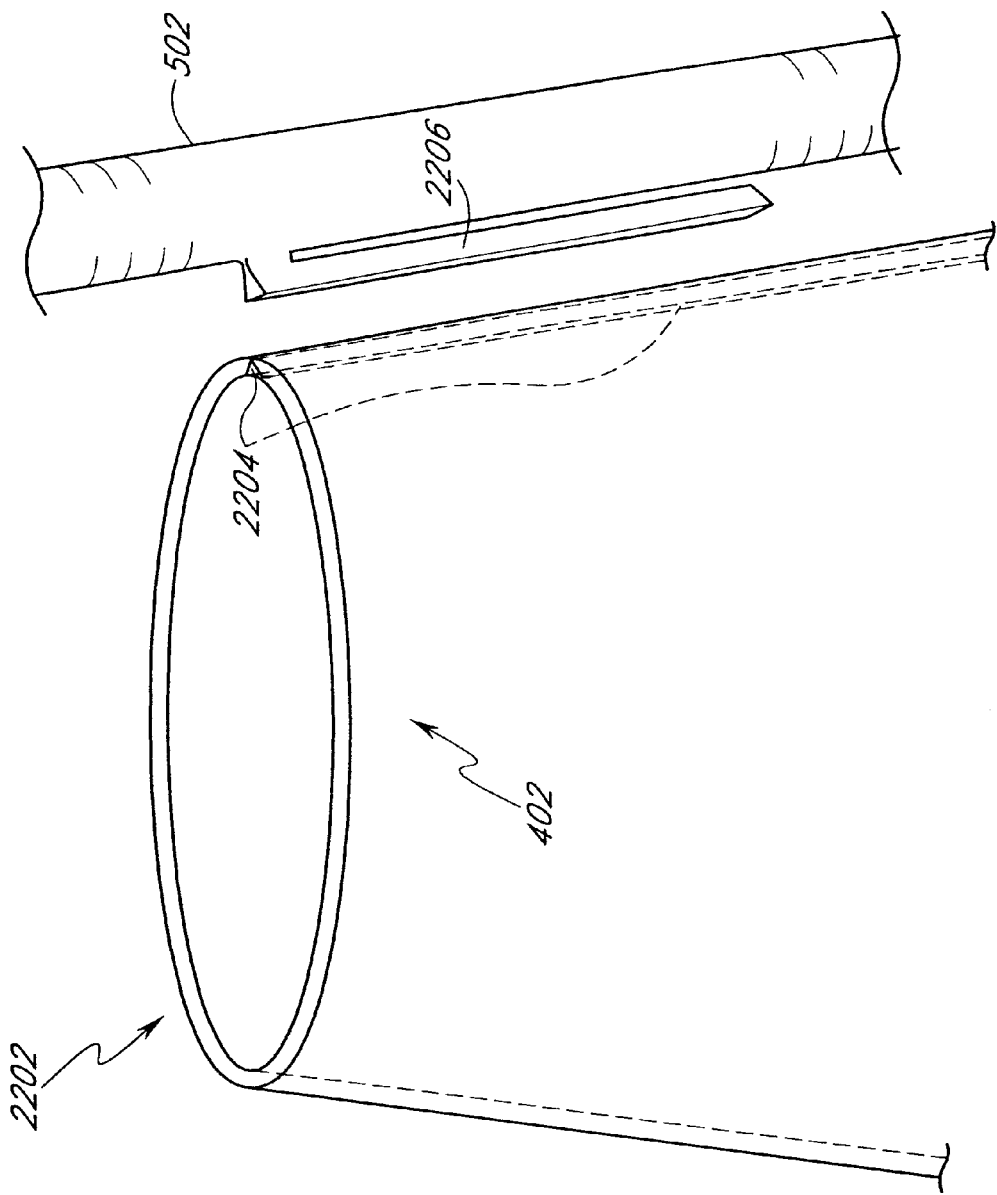
FIG. 22 illustrates an embodiment of the present invention wherein a modified nasal speculum attachment connects to a specimen access tube.

Additional embodiments of the present invention include embodiments wherein a modified nasal speculum attachment removably attaches to the specimen access tube 502. For example, FIG. 22 illustrates an embodiment of the present invention wherein a modified nasal speculum attachment 2202 connects to the specimen access tube 502.

The insertion surface 402 is formed to create a channel 2204 running along the inside of the insertion surface 402 in a direction substantially parallel to a central axis intersecting the holes 412 and 414 (FIG. 4). The channel 2204 slidably engages an attachment rod 2206 fixedly or otherwise attached to the specimen access tube 502.

Cross sections of the channel 2204 are preferably triangular, to securely engage the attachment rod 2206, which preferably also has triangular cross sections. Cross sections of the channel 2204 and the attachment rod 2206 may vary in shape so long as they are sufficiently similar to substantially fix the position of the specimen access tube 502 with respect to the nasal speculum attachment 2202.

The practitioner fits the attachment rod 2206 into the channel 2204, sliding a length of the attachment rod 2206 into the channel 2204. The attachment rod 2206 is made from a material sufficiently rigid to prevent substantial movement of the specimen access tube relative to the nasal speculum attachment 2202. The practitioner may then fit the nasal speculum attachment 2202 into the otoscope 302 and obtain a sinus specimen as described herein.

Figure 23:
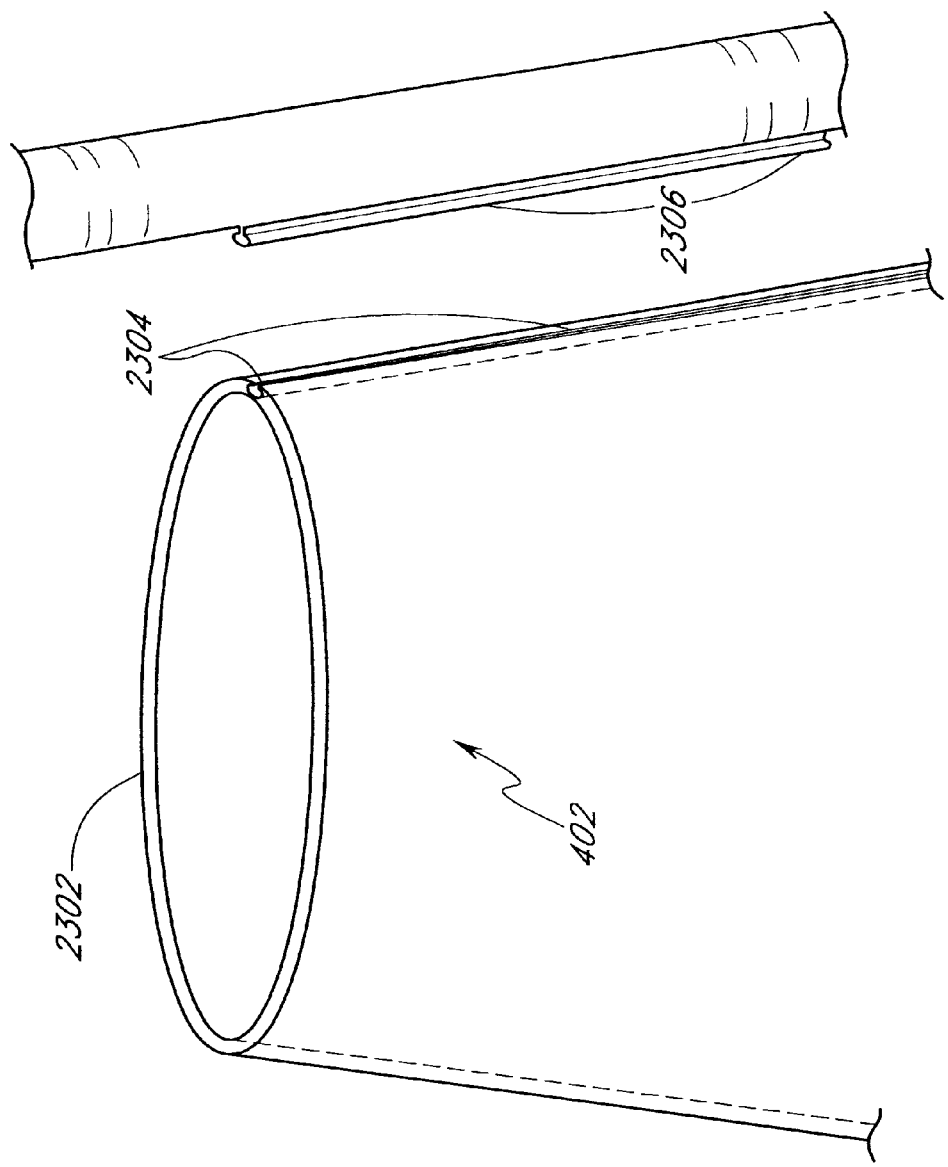
FIG. 23 illustrates another embodiment of the present invention wherein a modified nasal speculum attachment connects to a specimen access tube.

FIG. 23 illustrates another embodiment of the present invention wherein a modified nasal speculum attachment 2302 connects to the specimen access tube 502. The insertion surface 402 of the nasal speculum attachment 2302 is formed to create a channel 2304 running along the outside of the insertion surface 402 in a direction substantially parallel to a central axis intersecting the holes 412 and 414 (FIG. 4).

The channel 2304 comprises a substantially cylindrical space within the material of the insertion surface 402 and a slot. The slot runs the distance of the channel 2304 and has a width substantially smaller than the diameter of the circular cross section of the cylindrical space, and permits access to the cylindrical space from the outer surface of the insertion surface 402.

The channel 2304 slidably engages an attachment rod 2306 fixedly or otherwise attached to the specimen access tube 502. The attachment rod comprises a cylindrical rod having substantially circular cross-sections of the substantially the same dimension as the cross sections of the channel 2304, and a ridge member running the length of the cylindrical rod and connecting the cylindrical rod to the specimen access tube 502. Cross sections of the channel 2304 and the attachment rod 2306 may vary in shape so long as they are sufficiently similar to substantially fix the position of the specimen access tube 502 with respect to the nasal speculum attachment 2302.

The practitioner fits the attachment rod 2306 into the channel 2304, sliding a length of the attachment rod 2306 into the channel 2304. The attachment rod 2306 is made from a material sufficiently rigid to prevent substantial movement of the specimen access tube 502 relative to the nasal speculum attachment 2302. The practitioner may then fit the nasal speculum attachment 2302 into the otoscope 302 and obtain a sinus specimen as described herein.

Many other techniques exist for connecting a specimen access tube 502 to a modified nasal speculum adapter, such as many configurations involving holes, slots or channels in the nasal speculum adapter and conforming and engaging pins, rods or tabs on the specimen access tube 502. These techniques and others which clamp or grip the nasal speculum attachment to the specimen access tube 502 are specifically contemplated to be within the scope of the present invention.

Structures Avoiding Contamination

FIG. 24 illustrates a representation of a specimen access tube having an anti-contamination structure in accordance with an embodiment of the present invention. In this embodiment, the tip of the specimen access tube 502 at the insertion end 506 is flared to form an approximately olive-shaped tip 2402. The olive-shaped tip 2402 may be integrally formed onto or molded at the tip of the specimen access tube 502. Alternatively, the olive-shaped tip 2402 may be a separate structure having a substantially cylindrical internal passage of substantially the same diameter as the outer tubular diameter of the insertion end 506 tip of the specimen access tube 502, which may then be fixedly attached over the tip of specimen access tube 502.

The olive-shaped tip, being rounded in shape, does not substantially impede the introduction of the specimen access tube 502 into the middle meatus 208 area.

Moreover, the olive-shaped tip tends to spread apart tissues during that introduction, and advantageously directs material that could contaminate the specimen away from the hole 504 (FIG. 5) at the insertion end 506, thus increasing the chances of obtaining an uncontaminated specimen.

FIG. 25 illustrates another representation of a specimen access tube having an anti-contamination structure in accordance with an embodiment of the present invention. In this embodiment, the insertion end 506 tip of the specimen access tube is formed to have an approximately olive-shaped collection tip 2502, which may be integrally formed with or molded to the tubular insertion end 506 tip of the specimen access tube 502.

Alternatively, the olive-shaped collection tip 2502 could be a separate structure defining an internal cylindrical joining ring 2504 at a joining end 2506 having a diameter substantially the same as the outer tubular diameter of the insertion end 506 tip of the specimen access tube 502, which may then be positioned over the tip of specimen access tube 502 and fixedly attached thereon. The attachment may be accomplished by positioning the cylindrical joining ring 2504 over the tip of the specimen access tube 502 at a position along the shaft portion 514 whereat a rim 2508 at an insertion end 25010 of the olive-shaped collection tip 2502 is approximately coextensive with or extends just slightly beyond the tip of the specimen access tube 502. In that position, the cylindrical joining ring 2504 may be glued, cemented, welded, or friction fit to the shaft portion 514 of the specimen access tube. Alternatively, the cylindrical joining ring 2504 may be threaded to threadingly engage threads running from the tip of the specimen access tube 502 some distance along the shaft portion 514.

When the olive-shaped collection tip 2502 is attached to the specimen access tube 502 and introduced into a patient's nasal area toward the middle meatus 208 (FIG. 2), the olive-shaped collection tip 2502, being rounded, tends to separate tissues and direct potentially contaminating matter away from the tip of the specimen access tube 502. Moreover, the rim 2508 conducts some of the potentially contaminating matter along inner walls of a roughly spherical recess 2512 within the olive-shaped collection tip 2502 and between the inner walls of the olive-shaped collection tip 2502 and the outer walls of the specimen access tube 502. Thus, potentially contaminating matter may not contact the hole 504 or the tip of the specimen access tube 502 during insertion, advantageously reducing the possible that an obtained specimen would be contaminated.

FIG. 26 illustrates still another representation of a specimen access tube having an anti-contamination structure in accordance with an embodiment of the present invention. In this embodiment, the insertion end 506 tip of the specimen access tube is formed to have an approximately olive-shaped cage 2602, which may be integrally formed with or molded to the tubular insertion end 506 tip of the specimen access tube 502.

Alternatively, the olive-shaped cage 2602 could be a separate structure defining a cylindrical joining ring 2604 at a joining end 2606 having a diameter substantially the same as the outer tubular diameter of the insertion end 506 tip of the specimen access tube 502, which may then be positioned over the tip of specimen access tube 502 and fixedly attached thereon. The attachment may be accomplished by positioning the cylindrical joining ring 2604 over the tip of the specimen access tube 502 at a position along the shaft portion 514 whereat rounded prong tips 2608 attached via prongs 2610 to the cylindrical joining ring 2604 at an insertion end 2612 of the olive-shaped cage 2602 are approximately coextensive with or extend just slightly beyond the tip of the specimen access tube 502. In that position, the cylindrical joining ring 2604 may be glued, cemented, welded, or friction fit to the shaft portion 514 of the specimen access tube. Alternatively, the cylindrical joining ring 2604 may be threaded to threadingly engage threads running from the tip of the specimen access tube 502 some distance along the shaft portion 514.

A number of prongs 2610, preferably six (6), extend outwardly and upwardly from the cylindrical joining ring 2604 to define an approximately olive-shaped space within the prongs 2610. Each of the prongs 2610 terminates in an enlarged and rounded prong tip 2608.

When the olive-shaped cage 2602 is attached to the specimen access tube 502 and introduced into a patient's nostril toward the middle meatus 208 (FIG. 2), the prong tips 2608, being rounded, and the prongs 2610, being curved, tend to separate tissues and direct potentially contaminating matter away from the tip of the specimen access tube 502. Moreover, the prong tips 2608 conduct some of the potentially contaminating matter along the adjoining prongs 2610 away from the hole 504 and the tip of the specimen access tube. Therefore, potentially contaminating matter may not contact the hole 504 or the tip of the specimen access tube 502 during insertion, advantageously reducing the possible of contaminating a specimen with encountered during insertion.

FIG. 27 illustrates another embodiment of an anti-contamination structure in accordance with the present invention. An olive-shaped cage 2702 includes the six prongs 2610 connected to the cylindrical joining ring 2604 as described in relation to FIG. 26. The six prongs 2610 of the olive-shaped cage 2702 are, however, connected at their tips 2608 to the tip of the specimen access tube 502 at the insertion end 506.

It will be appreciated that other anti-contamination structures may be attached or formed with or to the specimen access tube 502 to reduce or eliminate the possibility of contamination. Anti-contamination structures may also assist in closing off the inside of the specimen access tube 502 during its insertion into a bodily orifice.

FIG. 28 illustrates an anti-contamination lid structure in accordance with an embodiment of the present invention. A lid 2802 is connected to the tip of the specimen access tube 502 at a hinge 2804. The hinge 2804 permits at least 90 degrees of rotational movement about its pin, allowing the lid 2802 to lay flat along the rim of the tip of the specimen access tube 502, and also allowing the lid to open an amount at least sufficient to allow an applicator to emerge directly from the tip with the lid having no effect on the direction of travel of the applicator. Such hinges are known in the art.

In use, the practitioner positions the specimen access tube 502 in place as described above. As the practitioner inserts the specimen access tube 502, the lid 2802 advantageously prevents entry of any contaminant into the specimen access tube. Once the tube 502 is positioned, the practitioner then slowly advances the applicator. As the applicator is advanced, it contacts the lid 2802 and pushes it open. When the applicator moves past the lid and contacts the specimen, the practitioner withdraws the applicator into the specimen access tube 502 and removes the specimen access tube 502 from the bodily orifice.

FIG. 29A illustrates another embodiment of an anti-contamination structure in accordance with the present invention. A thin sterile film 2902, circular in shape and having substantially the same diameter as the tip of the specimen access tube 502, is stretched taught and sealingly attached across the opening at the tip of the specimen access tube 502. That attachment is preferably performed by using a glue or cement presenting insubstantial medical risk to a patient when set.

Advantageously, the circular film 2902 is preferably formed to have scores 2904 (i.e., thin-walled or weakened crease lines) across its surface. When a force is applied against the surface of the film 2902, it tears first at the scores 2904. In a preferred embodiment, two score lines 2904 intersect the circular film 2902 at its center to form a cross.

FIG. 29B illustrates the use of an embodiment of the circular film anti-contamination structure. A practitioner advances the specimen access tube 502 into place. During that insertion, the circular film 2902 remains in place and advantageously prevents any contaminant from entering the specimen access tube 502.

Once the tube 502 is in place, the practitioner advances the applicator 2906 with a force sufficient to tear the circular film 2902 at the scores 2904. In a preferred embodiment, the force required to tear the film 2902 is sufficiently slight that the applicator can easily pierce the film. Thus, the practitioner need not force the applicator to a degree that tissue injury would occur when the applicator suddenly bursts through the film. The practitioner advances the applicator 2906 carefully to contact the specimen, and then withdraws the applicator 2906 into the tube. The specimen access tube 502 is then withdrawn.

FIG. 30A illustrates another anti-contamination structure in accordance with an embodiment of the present invention. A specimen access jacket 3002, made from a sterile thin film material, has an insertion end 3004 and an activation end 3006. The tip of the specimen access jacket 3002 includes a score 3008 as discussed above. The specimen access jacket 3002 is configured to form an elongated cylindrical space within the insertion of substantially the same dimension as the cylindrical form of specimen access tube 502 along the shaft portion 514.

The specimen access jacket 3002 is further configured to have a slit 3010 approximately midway down its length. The slit forms two activation tabs 3012 at the activation end 3006 of the specimen access jacket 3002.

FIG. 30B illustrates a representation of a specimen access jacket 3002 fit over a speculum access tube in an embodiment of the present invention. The shaft portion 514 of the specimen access tube 502 is substantially within and covered by the insertion end 3004 of the specimen access jacket 3002. The opening 508 at the collection end 510 of the specimen access tube 502 is accessible and not covered by the specimen access jacket 3002. Activation tabs 3012 extend down below the opening 508. The hole 412 at the insertion end 404 of the speculum attachment is not substantially obstructed by the specimen access jacket 3002, and, thus, the practitioner's visualization of matter within a bodily orifice is not hindered or impeded.

The practitioner inserts the specimen access tube 502 into the bodily orifice. During the insertion, the specimen access jacket 3002 advantageously prevents any contaminants from entering the specimen access tube 502. Once the tube 502 is in place, the practitioner grasps the activation tabs 3012 and tugs in a direction away from the insertion end 3004. Advantageously, the specimen access jacket 3002 tears at the score 308, recedes some distance down the shaft portion 514, and thus exposes the tip of the specimen access tube 502 to the specimen. The practitioner then advances the applicator carefully into contact with the specimen and then withdraws the applicator into the tube 502. Finally, the practitioner withdraws the specimen access tube 502. The specimen access jacket 3002 may be discarded.

Figure 31:
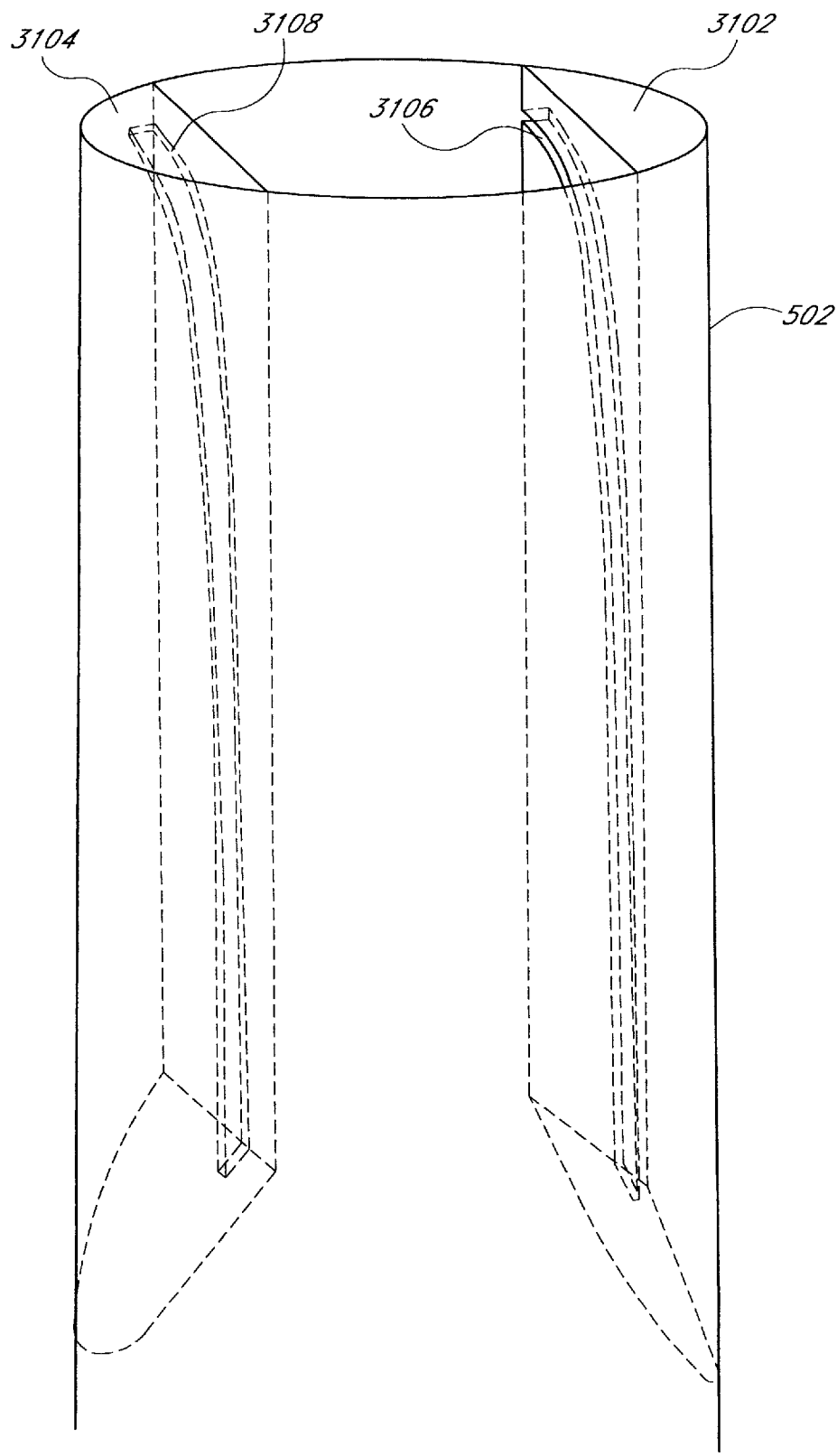
FIG. 31 illustrates a representation of the insertion end of a specimen access tube having contamination shield guides in accordance with an embodiment of the present invention.

FIG. 31 illustrates a representation of the insertion end of a specimen access tube having contamination shield guides in accordance with an embodiment of the present invention. First and second shield guide side walls 3102, 3104 have respective shield guide channels 3106, 3108 formed therein.

The first and second shield guide side walls 3102, 3104 are positioned across from each other within the inner cylindrical space defined within the tip of the specimen access tube 502.

FIG. 32 illustrates a perspective view of the first shield guide side wall 3102. The first shield guide wall is preferably a solid body, made of a rigid material such as plastic, forming generally a lengthwise portion of a cylinder. A curved surface 3202 fits snugly against the inner cylindrical wall of the specimen access tube 502. A flat surface 3204 is interrupted by the guide channel 3106. The guide channel 3106 runs from one side 3206 substantially near a top end 3208, in a curved pattern, down to a point substantially near a bottom end 3210. It will be appreciated that the second shield guide wall is constructed substantially the same, but having a guide channel 3108 formed in a mirror image manner to the guide channel 3106 to thereby match the curve of the same in location across from it.

FIG. 33 illustrates a side view of the shield guide side wall 3102. The bottom end 3210 defines a sloped surface 3302 rising from the bottom most point of the bottom end along the curved surface 3202 to a point defining the bottom edge of the flat surface 3204. The second side wall has a similar sloped surface (not shown). The sloped surface 3302 advantageously guides an applicator between the two shield guide side walls 3102, 3104 as it is begin advanced into the specimen access tube.

FIG. 34 illustrates a cross-sectional view through the shield guide side wall 3102. The curved surface 3202 represents an arc approximately one quarter of the circumference of the circle defined by a cross section of the specimen access tube 502.

Figure 35:
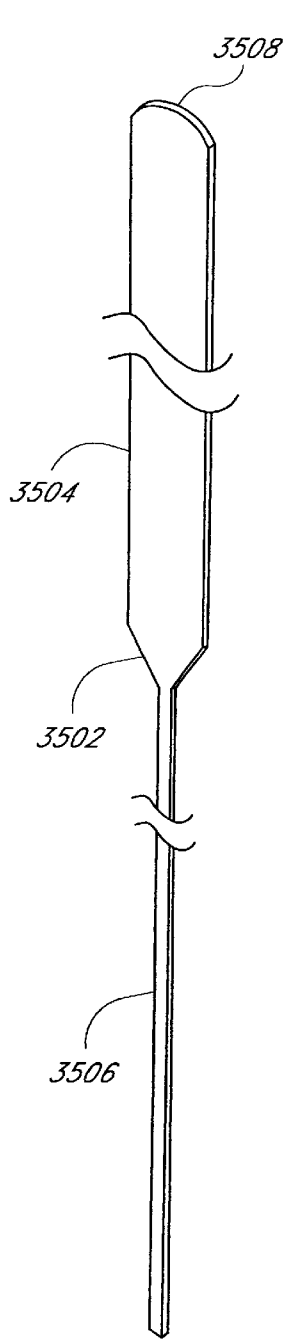
FIG. 35 illustrates a representation of an anti-contamination shield in accordance with an embodiment of the present invention.

FIG. 35 illustrates a representation of an anti-contamination shield. The anti-contamination shield 3502 has a shield blade 3504 and a shaft 3506. The shield 3502 is made from a flexible material that can bend substantially without deformation.

The shield blade 3504 is of a width spanning the distance between the guide channels 3106, 3108 when the side walls 3102, 3104 are positioned within the specimen access tube 502. The shield blade 3504 has a uniform thickness slightly less than the thickness of the guide channels 3106, 3108 so that the blade 3504 fits slidably within the channels 3106, 3108. The shield blade 3504 has a top edge 3508 curved to match the curvature of the inner wall of the specimen access tube 502 and to thereby substantially sealingly engage that inner wall.

The shield blade 3504 tapers into the shaft 3506. The shaft 3506 may be of the same thickness as the blade 3504, but is substantially narrower to advantageously occupy less room within the inner space of the specimen access tube 502, thereby permitting easier introduction and advancement of the applicator therein.

Figure 36:
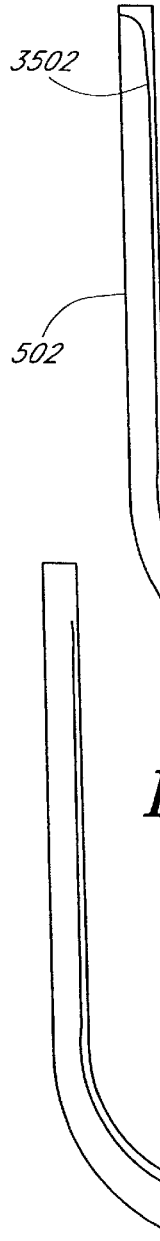
FIG. 36 illustrates the specimen access tube having a shield installed therein in accordance with an embodiment of the present invention.

FIG. 36 illustrates the specimen access tube 502 having the shield 3502 installed therein. As depicted and in a closed position, the shield 3502 substantially extends across a cross section of the tip of the specimen access tube. The shaft 3506 extends out of the specimen access tube 502 at the collection end 510.

Figure 37:
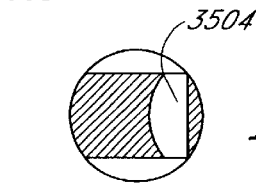
FIG. 37 represents a view looking into the tip of the specimen access tube with the shield blade substantially extending across a cross section at the tip of the tube.
Figures 38, 39:
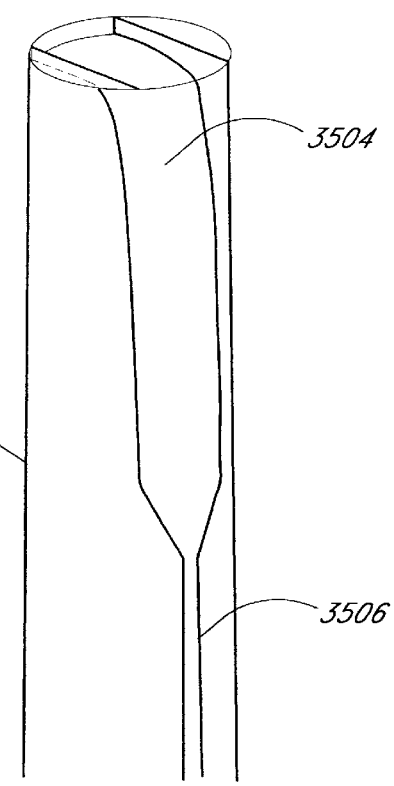
FIG. 38 illustrates a perspective view of the shield blade and shaft installed within the specimen access tube in the closed position.
FIG. 39 illustrates a representation of the specimen access tube having a shield installed therein in an open position.

FIG. 37 represents a view looking into the tip of the specimen access tube 502 with the shield blade 3504 substantially extending across a cross section at the tip of the tube 502, the top edge 3508 of the blade 3504 engaging the inner wall of the specimen access tube. FIG. 38 illustrates a perspective view of the shield blade 3504 and shaft 3506 installed within the specimen access tube 502 in the closed position.

FIG. 39 illustrates a representation of the specimen access tube 502 having a shield 3502 installed therein in an open position. The shaft 3506, when pulled out of the specimen access tube 502 a small distance, causes the blade 3504 to slide along the guide channels 3106, 3108 to a position leaving the tip of the specimen access tube 502 substantially open.

Figure 40:
FIG. 40 illustrates a view looking into the specimen access tube when the blade is in an open position.

FIG. 40 illustrates a view looking into the specimen access tube 502 when the blade 3504 is in an open position. The blade 3504 occupies little of the cross section at the tip of the specimen access tube 502 when it is in the open position.

In using this embodiment, a practitioner advances the shaft 3506 of the blade 3502 into the specimen access tube 502 to ensure that the blade is in a closed position. The practitioner then advances an applicator into the specimen access tube 502 to a point just behind the blade 3504 at the tip of the specimen access tube 502. Next, the practitioner inserts the tube 502 into the bodily orifice. Advantageously, the blade prevents any matter from contaminating the applicator during the insertion.

When the specimen access tube 502 is in place, the practitioner pulls the shaft 3506 a small distance out of the tube 502 to slide the blade 3504 down and into an open position. It will be appreciated that the shaft 3506 could be color coded such that when only a red portion of the shaft extends out of the specimen access tube, the blade is in a closed position. When a yellow portion also extends out, then the blade is partially open. When a red portion appears outside the tube 502, the blade 3504 is fully open.

With the blade 3504 in an open position, the practitioner advances the applicator to contact a specimen and then withdraws the applicator back into the specimen access tube 502. The practitioner may then push the shaft 3506 to put the blade 3504 in a closed position and then withdraw the specimen access tube 502.

This invention may be embodied in other specific forms without departing form the essential characteristics as described herein. The embodiments described above are to be considered in all respects as illustrative only and not restrictive in any manner. The scope of the invention is indicated by the following claims rather than by the foregoing description. Any and all changes which come within the meaning and range of equivalency of the claims are to be considered within their scope.

What is claimed is:

1. An apparatus for obtaining a specimen through a bodily orifice of an animal, the apparatus comprising:

a speculum having an insertion end and a viewing end, said speculum defining a visualization path from said viewing end and through said insertion end, said speculum permitting visualization at said viewing end and along said visualization path of matter within said orifice when said insertion end is positioned in an opening of said orifice;

a specimen access tube having an insertion end and a collection end, said specimen access tube operably connected to said speculum in an arrangement wherein said insertion end of said specimen access tube enters said orifice during said visualization, said specimen access tube defining a collection path from said collection end and through said insertion end of said specimen access tube, said specimen access tube providing access from said collection end through said collection path to a specimen within said orifice proximate to said insertion end of said specimen access tube; and anti-contamination means substantially preventing matter in said orifice from entering said collection path as said specimen access tube enters said orifice.

2. The apparatus as described in claim 1, wherein said collection end of said specimen access tube remains outside said bodily orifice during said visualization and while said access to said specimen is provided.

3. The apparatus as described in claim 1, wherein said collection path provides access to said specimen in a manner substantially avoiding contact with matter along bodily surfaces inside said orifice during said access.

4. The apparatus as described in claim 1, wherein at least a portion of said specimen access tube is substantially viewable from said viewing end of said speculum via said visualization path.

5. The apparatus as described in claim 1, wherein a portion of said specimen access tube is located within a space defined by said speculum.

6. The apparatus as described in claim 1, wherein said speculum is a standard speculum attachment.

7. An apparatus for obtaining a specimen through a bodily orifice of an animal, the apparatus comprising:

a speculum having an insertion end and a viewing end, said speculum defining a visualization path from said viewing end and through said insertion end, said speculum permitting visualization at said viewing end and along said visualization path of matter within said orifice when said insertion end is positioned in an opening of said orifice;

a specimen access tube having an insertion end and a collection end, said specimen access tube operably connected to said speculum in an arrangement wherein said insertion end of said specimen access tube enters said orifice during said visualization, said specimen access tube defining a collection path from said collection end and through said insertion end of said specimen access tube, said specimen access tube providing access from said collection end through said collection path to a specimen within said orifice proximate to said insertion end of said specimen access tube; and a speculum attachment ring fitting substantially securely around said speculum, said speculum attachment ring holding said specimen access tube in a first position relative to said speculum permitting said access to said specimen, and said speculum attachment ring manipulable to allow said specimen access tube to be located in a second position relative to said speculum permitting said speculum attachment ring to be fit around said speculum.

8. The apparatus as described in claim 7, wherein said animal is human.

9. The apparatus as described in claim 8, wherein said orifice is proximate to a human nose.

10. The apparatus as described in claim 9, wherein said specimen is located in a middle meatus region of a human.

11. An apparatus for obtaining a specimen through a bodily orifice of an animal, the apparatus comprising:

a speculum having an insertion end and a viewing end, said speculum defining a visualization path from said viewing end and through said insertion end, said speculum permitting visualization at said viewing end and along said visualization path of matter within said orifice when said insertion end is positioned in an opening of said orifice;

a specimen access tube having an insertion end and a collection end, said specimen access tube operably connected to said speculum in an arrangement wherein said insertion end of said specimen access tube enters said orifice during said visualization, said specimen access tube defining a collection path from said collection end and through said insertion end of said specimen access tube, said specimen access tube providing access from said collection end through said collection path to a specimen within said orifice proximate to said insertion end of said specimen access tube; and anti-contamination means substantially separating matter in said orifice from said collection path during said entry of said specimen access tube into said orifice.

12. The apparatus as described in claim 11, wherein said anti-contamination means is an approximately olive-shaped structure connected at a tip of the specimen access tube at said insertion end.

13. The apparatus as described in claim 11, wherein said anti-contamination means includes a thin film covering an opening in said specimen access tube at said insertion end.

14. A method for obtaining a specimen from a bodily orifice of an animal, said method comprising the steps of:

advancing an insertion end of a specimen access tube into said bodily orifice such that a tip of said specimen access tube at said insertion end comes to rest proximate to a specimen in said bodily orifice;

viewing through a speculum at least a portion of said advancing of said insertion end into said bodily orifice, said speculum operably connected to said specimen access tube; and advancing a head of an applicator into a collection end of said specimen access tube and through said tip such that said head contacts and holds said specimen, wherein an anti-contamination means prevents substantial contact between said applicator head and matter in said bodily orifice other than said specimen.

15. The method as described in claim 14, said method comprising the further step of:

withdrawing said specimen access tube from said bodily orifice.

16. The method as described in claim 15, said method comprising the further step of:

withdrawing said applicator head from said specimen access tube.

17. The method as described in claim 16, said method comprising the further step of:

placing said applicator head in a standard culture medium.

18. The method as described in claim 14, wherein said speculum is removably connected to said specimen access tube.

19. The method as described in claim 14, wherein said anti-contamination means is a thin film stretched across said tip of said insertion end of said specimen access tube and wherein said advancing of said applicator head pierces said thin film, said thin film substantially preventing matter in said bodily orifice from entering said specimen access tube during said advancing of said insertion end of said specimen access tube.

20. The method as described in claim 14, wherein said anti-contamination means is a thin film specimen access jacket enveloping a substantial portion of said insertion end of said specimen access tube, said specimen access jacket having at least one activation tab which operates when pulled to tear open a tip of said specimen access jacket covering said tip of said specimen access tube, said specimen access jacket substantially preventing matter in said bodily orifice from entering said specimen access tube during said advancing of said insertion end of said specimen access tube, said method comprising the further step of:

pulling said activation tab of said specimen access jacket before said step of advancing said head of said applicator.

21. The method as described in claim 14, wherein said anti-contamination means is a slideable shield and wherein a blade portion of said slideable shield slides to a closed position to substantially close a hole at said tip of said insertion end of said specimen access tube and slides to an open position to substantially open said hole, wherein said slideable shield has a shaft portion extending out of the collection end of said specimen access tube, said shaft portion manipulable to cause said blade portion to open or close said hole, said method comprising the further step of:

manipulating said shaft to substantially open said hole before said step of advancing said head of said applicator.

22. A specimen access device, comprising:

collection means for providing a specimen collection path extending from outside a bodily orifice to a position proximate to a specimen in said bodily orifice;

a speculum attachment operably connected to said collection means to provide visualization of a portion of said collection means in said bodily orifice; and anti-contamination means substantially separating said collection means from matter in said bodily orifice other than said specimen.

23. The apparatus as described in claim 22, wherein said collection means is a specimen access tube having an insertion end that is adapted to be inserted into said bodily orifice, and wherein said anti-contamination means is a thin film stretched across a tip of said insertion end of said collection means.

24. The apparatus as described in claim 22, wherein said collection means is a specimen access tube having an insertion end that is adapted to be inserted into said bodily orifice, and wherein said anti-contamination means includes an approximately olive-shaped tip on said insertion end of said collection means.

25. The apparatus as described in claim 22, wherein said collection means includes a tubular shaft with an inner wall and an outer wall, said tubular shaft having an insertion end that is adapted to be inserted into said bodily orifice, and wherein said anti-contamination means is an approximately olive-shaped collection tip surrounding said insertion end of said tubular shaft, said collection tip having an inner wall and an outer wall such that when said collection tip is positioned around said insertion end of said tubular shaft, a recess is formed between said outer wall of said tubular shaft at said insertion end and said inner wall of said collection tip.

26. The apparatus as described in claim 22, wherein said anti-contamination means is a thin film specimen access jacket.

27. The apparatus as described in claim 22, wherein said collection means includes a tubular shaft with an inner wall and an outer wall, said tubular shaft having an insertion end that is adapted to be inserted into said bodily orifice, and wherein said anti-contamination means includes an approximately olive-shaped cage fitting on said insertion end of said tubular shaft, said cage having a base and multiple prongs extending upward from said base, said multiple prongs extending over a hole at said insertion end of said tubular shaft to direct potentially contaminating matter away from said hole.

28. The apparatus as described in claim 22, wherein said collection means includes a tubular shaft having an insertion end adapted to be inserted into said bodily orifice, said insertion end having a hole permitting access to said specimen, and wherein said anti-contamination means includes a lid structure movable between a first closed position substantially covering said hole and a second open position substantially uncovering said hole.

29. The apparatus as described in claim 22, wherein said collection means includes an insertion end that is adapted to be inserted into said bodily orifice and a collection end, and wherein said anti-contamination means is a slideable shield having a blade portion that slides to a closed position to substantially close a hole at said insertion end of said specimen access tube and slides to an open position to substantially open said hole, said slideable shield having a shaft portion extending out of said collection end of said specimen access tube, said shaft portion manipulatable to cause said blade portion to open or close said hole.

* * * * *